(12) United States Patent
Burnett et al.

(10) Patent No.: US 6,903,123 B2
(45) Date of Patent: Jun. 7, 2005

(54) AZETIDINYL DIAMINES USEFUL AS LIGANDS OF THE NOCICEPTIN RECEPTOR ORL-1

(75) Inventors: Duane A. Burnett, Bernardsville, NJ (US); Mary Ann Caplen, Sayreville, NJ (US); Michael F. Czarniecki, Watchung, NJ (US); Martin S. Domalksi, Verona, NJ (US); Ginny D. Ho, Murray Hill, NJ (US); Deen Tulshian, Lebanon, NJ (US); Wen-Lian Wu, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/770,758

(22) Filed: Feb. 3, 2004

(65) Prior Publication Data

US 2004/0157822 A1 Aug. 12, 2004

Related U.S. Application Data

(62) Division of application No. 10/294,814, filed on Nov. 14, 2002, now abandoned.
(60) Provisional application No. 60/332,284, filed on Nov. 16, 2001.

(51) Int. Cl.[7] .................. C07D 401/00; A61K 31/40
(52) U.S. Cl. .............. 514/340; 514/408; 546/268.1; 548/950
(58) Field of Search .................................. 548/950

(56) References Cited

U.S. PATENT DOCUMENTS

| | | | |
|---|---|---|---|
| 4,052,383 A | | 10/1977 | Gold et al. |
| 4,196,124 A | * | 4/1980 | Gold et al. .................. 548/950 |
| 5,710,155 A | | 1/1998 | Schnorrenberg et al. |

FOREIGN PATENT DOCUMENTS

| | | | |
|---|---|---|---|
| WO | WO 96/32386 | 10/1996 | |
| WO | WO 00/06545 | 2/2000 | |
| WO | WO 01/07050 | 2/2001 | ......... A61K/31/445 |

OTHER PUBLICATIONS

Fawzi et al, *Eur. J. Pharmacology*, 336 (1997), p. 233–242.
Hey, Bolser et al, *Brit. J. Pharmacology*, 114 (1995), p. 735–738.
West et al, *Molecular Pharmacology*, 38 (1990), p. 610–613.

* cited by examiner

*Primary Examiner*—Kamal Saeed
(74) *Attorney, Agent, or Firm*—Anita W. Magatti

(57) ABSTRACT

Disclosed are nociceptin ORL-1 receptor agonists of the formula

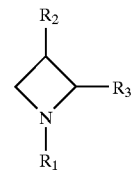

wherein:
(a) $R_1$ is optionally substituted alkyl, fluorenyl, pyrimidinyl or optionally substituted piperidinyl;
$R_2$ is H; and $R_3$ is —C(H)(R)—$NR_7R_8$;
R is H, optionally substituted aryl or arylalkyl, or heteroaryl;
$R_7$ is —$(CH_2)_xR_9$, optionally substituted tetrahydronaphthyl, or cycloalkyl; and $R^8$ is H;
or $R_7$ and $R_8$ together form a substituted piperidinyl or piperazinyl ring;
x is 0–10; and
$R_9$ is H, alkoxy, optionally substituted phenyl, naphthyl, heteroaryl, pyrrolidinyl, pyrrolidonyl, optionally substituted piperidinyl or diphenylmethyl; or
(b) $R_2$ is —$NHR_7$ or

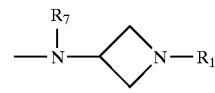

and $R_3$ is H;
pharmaceutical compositions; and methods of using the compounds to treat cough and pain.

14 Claims, No Drawings

AZETIDINYL DIAMINES USEFUL AS LIGANDS OF THE NOCICEPTIN RECEPTOR ORL-1

CROSS REFERENCE TO RELATED APPLICATION

This application is a divisional of U.S. Ser. No. 10/294,814, filed Nov. 14, 2002 now abandoned, which claims the benefit of U.S. Provisional Application No. 60/332,284, filed Nov. 16, 2001.

BACKGROUND OF THE INVENTION

The G protein coupled nociceptin receptor known as ORL1 has been shown to be involved in the modulation of pain in animal models. It bears high homology to the classic opioid receptors ($\mu$, k, $\delta$), but has little cross reactivity with their native ligands. Current opioid analgesics target these classic opioid receptors, but have limiting side effect profiles (e.g. tolerance, physical dependence, respiratory depression and decrease of gastrointestinal function). ORL1 receptors are colocalized in regions of the CNS similar to the opioid receptors, as well as in the periphery.

Nociceptin, the endogenous ligand to ORL1, was discovered in 1995 and shown to be a peptide ligand that activates the ORL1 receptor, but not the classic opioid receptors. Initial reports have suggested that nociceptin and the ORL1 receptor are involved in a newly discovered pathway involved in the perception of pain. Further reports have shown nociceptin to be analgesic when administered intrathecally to rodents. The in vivo efficacy of nociceptin in animal models of pain is similar to that of the endogenous opioids. Nociceptin is also reported to act as an anxiolytic agent when administered into the brains of rodents. The in vivo efficacy in rodent anxiety models is similar to classic benzodiazepine anxiolytics. In addition, nociceptin has been recently reported to inhibit capsaicin induced bronchoconstriction in isolated guinea pig lung tissue, suggesting a role for ORL1 agonists in the treatment of cough. Together, these data suggest that nociceptin receptor agonists may have significant analgesic, anxiolytic, or antitussive properties.

SUMMARY OF THE INVENTION

Compounds of the invention are represented by formula I:

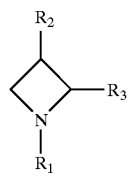

I or a pharmaceutically acceptable salt or solvate thereof, or a diastereomer or enantiomer thereof, wherein:

(a) $R_1$ is —$(CH_2)_n CHR_4 R_5$, fluorenyl, pyrimidinyl or

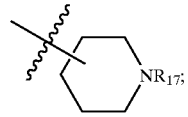

n is 0, 1, 2 or 3;

$R_2$ is H; and $R_3$ is —C(H)(R)—$NR_7 R_8$;

R is H, aryl, $R_6$-aryl, aryl$(CH_2)_{1-2}$, $R_6$-aryl$(CH_2)_{1-2}$ or heteroaryl;

$R_4$ is H, aryl, $R_6$-aryl, heteroaryl, $C_{1-6}$ alkyl, $C_{3-6}$ cycloalkyl or $C_{2-6}$ alkenyl;

$R_5$ is aryl, $R_6$-aryl, heteroaryl, $C_{1-6}$ alkyl, $C_{3-6}$ cycloalkyl, $C_{2-6}$ alkenyl or fluorenyl, provided that when $R_4$ and $R_5$ are each phenyl, R is not phenyl or $R_6$-phenyl;

or $R_4$ is H and $R_5$ is tetrahydronaphthyl or tetrahydronaphthyl substituted with 1 or 2 substituents selected from the group consisting of halogen, $C_{1-6}$ alkoxy, hydroxy, $C_{1-6}$ alkyl and trihalo($C_{1-6}$)alkyl;

$R_6$ is 1 or 2 substituents independently selected from the group consisting of halogen, $C_{1-6}$ alkoxy, hydroxy, phenyl, phenoxy, $C_{1-6}$ alkyl, trihalo($C_{1-6}$)alkyl, amino, amido, —$NO_2$, naphthyl, benzoyl and benzyloxy, or 2 adjacent ring carbon atoms can be substituted by methylenedioxy;

$R_7$ is —$(CH_2)_x R_9$, tetrahydronaphthyl, tetrahydronaphthyl substituted with 1 or 2 $R_{10}$ groups, or $C_5$–$C_7$ cycloalkyl; and $R^8$ is H;

or $R_7$ and $R_8$ together form a ring of the formula

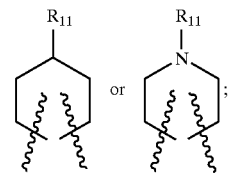

x is 0 to 10;

$R_9$ is H, $C_1$–$C_6$ alkoxy, phenyl, phenyl substituted with 1 or 2 $R_{10}$ groups, naphthyl, pyridyl, imidazolyl, furanyl, pyrrolidinyl, pyrrolidonyl, piperidinyl, N—($C_1$–$C_6$ alkyl)-piperidinyl, N-aryl($C_1$–$C_6$ alkyl)piperidinyl or diphenylmethyl;

$R_{10}$ is independently selected from the group consisting of halogen, $C_1$–$C_6$ alkoxy, $C_1$–$C_6$ alkyl, —$OCF_3$ and methylenedioxy;

$R_{11}$ is aryl($C_1$–$C_6$)alkyl, di-aryl($C_1$–$C_6$)alkyl or piperidinyl; and $R_{17}$ is H, $C_1$–$C_6$ alkyl or benzyl; or (b) $R_2$ is —$NHR_7$ or

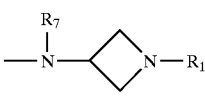

and $R_3$ is H; and $R_1$ and $R_7$ are as defined in (a).

In another aspect, the invention relates to a pharmaceutical composition comprising at least one compound of formula I and a pharmaceutically acceptable carrier.

The compounds of the present invention are agonists of the ORL-1 receptor, and therefore, in another aspect, the invention relates to a method of treating cough, pain, anxiety, asthma, alcohol abuse or depression, comprising administering to a mammal in need of such treatment an effective amount of at least one compound of formula I.

In another aspect, the invention relates to a method of treating cough, comprising administering to a mammal in need of such treatment: (a) an effective amount of at least one compound of formula I; and (b) an effective amount of one or more additional agents for treating cough, allergy or asthma symptoms selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists.

In still another aspect, the invention relates to a pharmaceutical composition comprising at least one compound of formula I and one or more additional agents selected from the group consisting of: antihistamines, 5-lipoxygenase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$, and $NK_3$, tachykinin receptor antagonists, and $GABA_B$ agonists.

DETAILED DESCRIPTION

Referring to formula I above, preferred are compounds of (a) or (b) wherein $R_1$ is —$(CH_2)_n CHR_4 R_5$ and n is 0 or 1, more preferably 0. $R_4$ is preferably aryl, $R_6$-aryl or heteroaryl, more preferably phenyl, $R_6$-phenyl or pyridyl. $R_5$ is preferably aryl or $C_1$–$C_6$ alkyl, more preferably phenyl, $R_6$-phenyl or $C_2$–$C_5$ alkyl, provided both $R_4$ and $R_5$ are not phenyl when R is optionally substituted phenyl. When $R_6$ is a substituent on $R_4$ or $R_5$, it is preferably halogen, especially fluoro.

Preferred are compounds of formula I (a), i.e., those wherein $R_2$ is H and $R_3$ is —C(H)(R)—$NR_7 R_8$. R is preferably $R_6$-phenyl, benzyl or $R_6$-benzyl. When $R_6$ is a substituent on R, it is preferably 1 or 2 substituents independently selected from the group consisting of —$CF_3$, halogen, benzyloxy and —$CH_3$, wherein halogen is preferably chloro or fluoro. $R_7$ and $R_8$ are preferably each H.

As used herein, the following terms are used as defined below unless otherwise indicated:

alkyl represents straight and branched carbon chains containing from 1 to 6 carbon atoms, for example methyl, ethyl, propyl, iso-propyl, n-butyl, t-butyl, n-pentyl, isopentyl, hexyl and the like;

alkenyl represents an alkyl chain of 2 to 6 carbon atoms comprising one or two double bonds in the chain, e.g., vinyl, propenyl or butenyl;

alkoxy represents an alkyl moiety covalently bonded to an adjacent structural element through an oxygen atom, for example, methoxy, ethoxy, propoxy, butoxy, pentoxy, hexoxy and the like;

aryl represents a monoaromatic ring or a bicyclic fused carbocyclic ring system of 6- to 10 carbon atoms, for example phenyl and naphthyl;

cycloalkyl represents saturated carbocyclic rings of from 3 to 7 carbon atoms, as specified in the definitions;

halo represents fluoro, chloro, bromo and iodo;

heteroaryl means a single ring heteroaromatic group of 5 to 6 atoms comprised of 2 to 5 carbon atoms and 1 to 3 heteroatoms independently selected from the group consisting of N, O and S, provided that the rings do not include adjacent oxygen and/or sulfur atoms. Examples of single-ring heteroaryl groups are pyridyl, oxazolyl, isoxazolyl, oxadiazolyl, furanyl, pyrrolyl, thienyl, imidazolyl, pyrazolyl, thiazolyl, isothiazolyl, thiadiazolyl, pyrazinyl, pyrimidyl, pyridazinyl and triazolyl. N-Oxides are also contemplated, e.g. pyridyl N-oxide.

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of formula I can be prepared using procedures known in the art. For example, compounds of formula I wherein $R_3$ is —C(H)(R)—$NR_7 R_8$, wherein $R_7$ and $R_8$ are each H and R is $R_6$-phenyl can be prepared according to the following overall synthetic scheme:

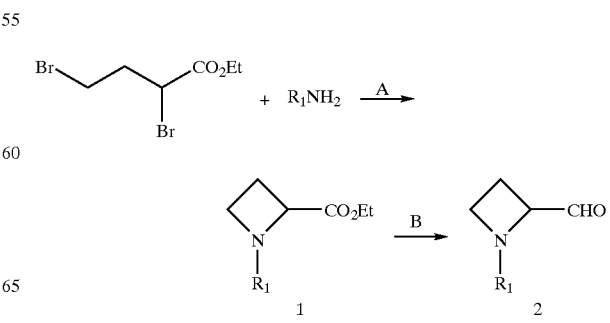

-continued
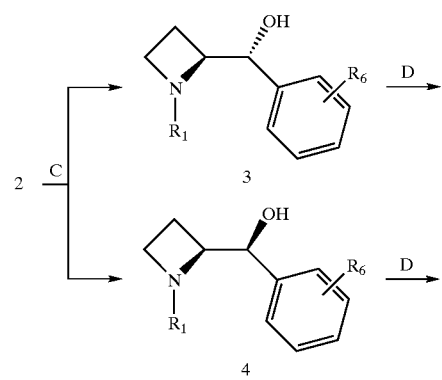
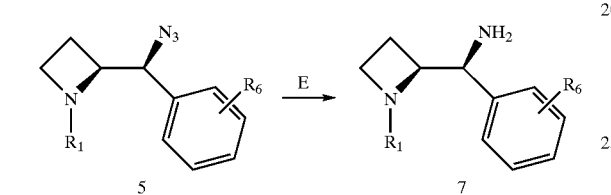
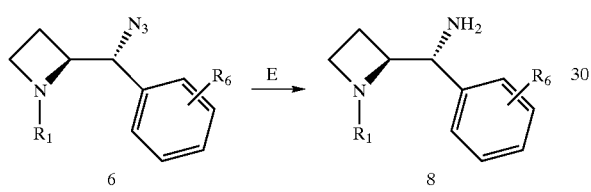
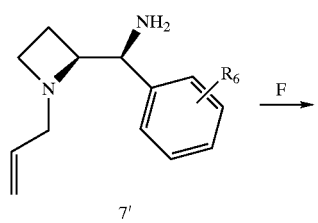
7'
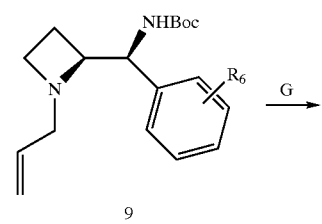
9
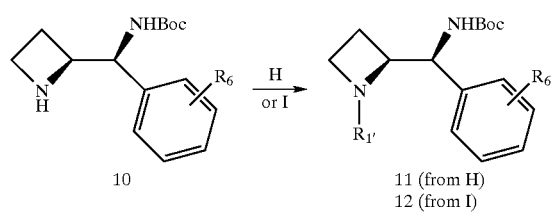
10    11 (from H)
      12 (from I)
-continued
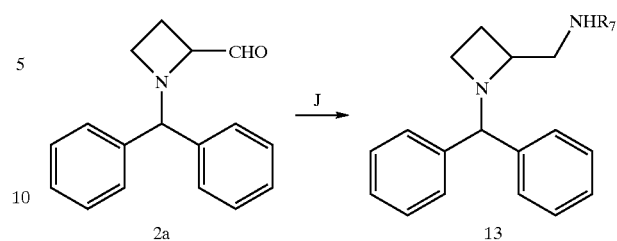
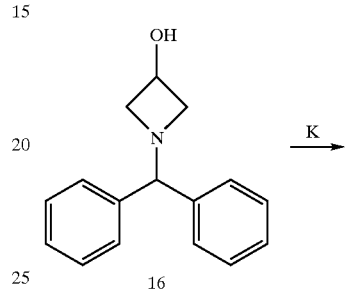
16
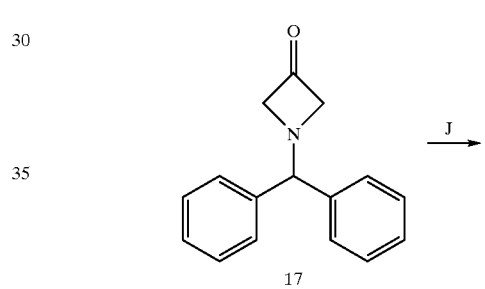
17
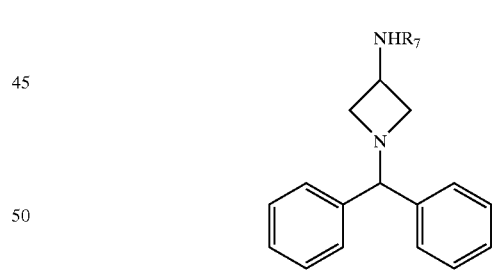
14
and/or
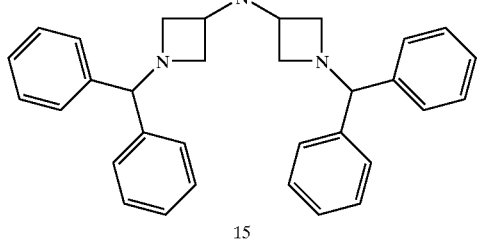
15

When $R_6$ is an amino or hydroxy group, it must be protected by a suitable protecting group by a method well known in the art.

Following are details of the steps (A–K) in the above procedure. The procedures are exemplified for specific compounds, but those skilled in the art will recognize that other compounds of formula I can be made by similar procedures.

The following abbreviations are used in this application: RT (room temperature); $Et_2O$ (ether); EtOAc (ethyl acetate); Ph (phenyl); Et (ethyl); and TFA (trifluoroacetic acid).

Step A:

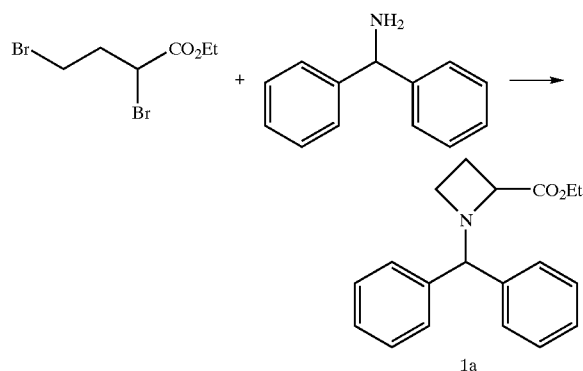

1a

To a solution of ethyl 2,4-dibromobutyrate (36.31 g, 0.132 mol) in $CH_3CN$ (140 ml) was added aminodiphenylmethane (73.59 g, 0.402 mol). The solution was stirred at RT for 1 h, then heated to 55° C. for 20 h. The suspension was cooled to RT and the precipitated salt was collected by filtration and washed with $Et_2O$. The combined filtrate and $Et_2O$ washings were concentrated in vacuo and the residue dissolved in $Et_2O$ (400 ml). The solution was washed with saturated $NaHCO_3$ (100 ml) and the wash was extracted with $Et_2O$ (2×100 ml). The combined ethereal solutions were washed with saturated NaCl (100ml), dried over $MgSO_4$, and concentrated in vacuo to give 49.99 g of an oil which slowly solidified. This material was purified by $SiO_2$ chromatography eluting with 2% EtOAc in hexanes progressing to 10% EtOAc in hexanes. Concentration of the appropriate fractions gave 25.67 g (66%) of the desired product as a white solid. MS: calcd for $C_{19}H_{21}NO_2.H^+$ m/z=296.16, observed m/z=296.1 $(M+1)^+$.

The following compounds were prepared by an analogous procedure:

| Prep. | $R_1$ | Analytical Data |
|---|---|---|
| 1b | $PhCH_2$ | MS calcd for $C_{13}H_{17}NO_2.H^+$ m/z=220.1 observed m/z=220 $(M+1)^+$ |
| 1c | $CH_2$=$CHCH_2$ | MS calcd for $C_9H_{15}NO_2.H^+$ m/z=170.1 observed m/z=170 $(M+1)^+$ |

Step B:

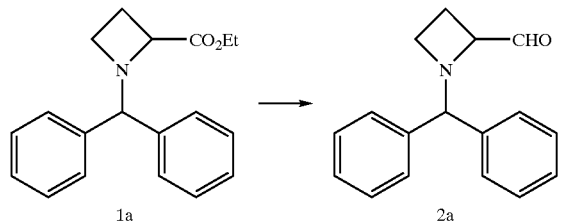

1a    2a

To a stirred solution of 1a (7.00 g, 23.7 mmol) in dry THF (50 ml) at −75° C. under Ar was added a cooled (−78° C.) 1M solution of DiBAL-H in toluene (28.4 ml, 28.4 mmol) dropwise via a cannula over ~1 h. The reaction was stirred for 1 h at −70° C. It was quenched by the careful addition of several small portions of $Na_2SO_4.(H_2O)_{10}$. The reaction was stirred at RT, then diluted with EtOAc (200 ml). It was filtered through Celite and concentrated in vacuo to give 5.98 g of a white solid. This material was triturated with 10% EtOAc in hexanes to give the desired aldehyde 2a as a white solid (3.09 g, 52%). MS: calc'd for $C_{17}H_{17}NO.H^+$ m/z=252.14, observed m/z=252.20 $(M+1)^+$.

The following compounds were prepared by an analogous procedure:

| Prep. | $R_1$ | Analytical Data |
|---|---|---|
| 2b | $PhCH_2$ | $^1H$ NMR(400MHz, $CDCl_3$)δ 9.47(d, J=3.9Hz, 1H, CHO), 7.25–7.40(m, 5H, Ph), 3.60–3.90(m, 3H), 2.95–3.30(m, 2H), 2.00–2.40(m, 2H) |
| 2c | $CH_2$=$CHCH_2$ | $^1H$ NMR(400MHz, $CDCl_3$)δ 9.73(d, J=2.6Hz, 1H, CHO), 5.75–5.90(m, 1H), 5.10–5.30(m, 2H), 2.90–3.80(m, 5H), 2.00–2.40(m, 2H) |

Step C:

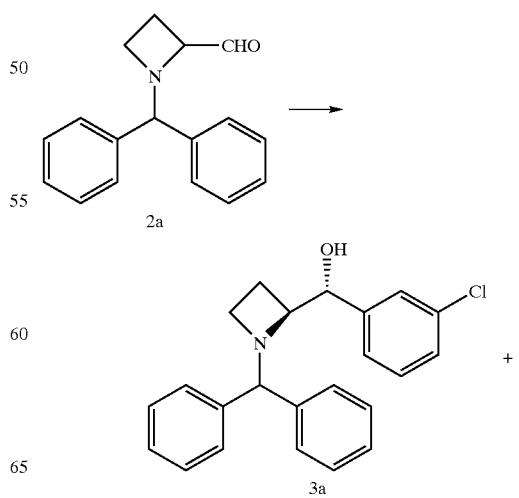

2a

3a

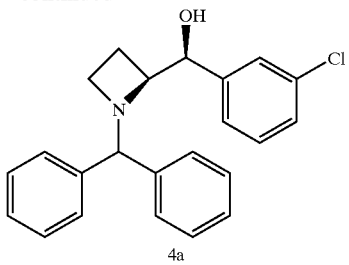

4a

A solution of 2a (15.00 g, 59.7 mmol) in dry THF(75 ml) was cooled to −40° C. under N₂. To this solution was added a 0.5M solution of 3-chlorophenylmagnesium-bromide (155.2 ml, 77.6 mmol) in THF dropwise over 1.25 h. The reaction was stirred with gradual warming to 0° C. over 2.5 h. The reaction was quenched by the dropwise addition of water (20 ml) while maintaining the 0° C. temperature. The reaction was warmed to RT and additional water (150 ml) was added. The solution was extracted with EtOAc (2×700 ml). The combined EtOAc layers were washed with brine (200 ml) and dried over Na₂SO₄. The solvent was removed in vacuo to give 20.78 g of a semisolid residue. This residue was recrystallized from EtOH to give 8.76 g of the erythro isomer 3a as a white solid. The mother liquor was concentrated to give an orange oil. The resulting oil was purified by flash chromatography over 500 g of SiO₂, eluting with a gradient of 3% EtOAc in hexanes, progressing slowly to 18% EtOAc in hexanes. The less polar erythro isomer 3a eluted first to give another 3.61 g, followed by 4.20 g of the more polar threo isomer 4a.

Analytical data for 3a: MS calcd for $C_{23}H_{22}ClNO.H^+$ m/z=364.15, observed m/z=364.1 (M+1)⁺. Analytical data for 4a: MS calcd for $C_{23}H_{22}ClNO.H^+$ m/z=364.15, observed m/z=364.35 (M+1)⁺.

The following compounds were prepared by an analogous procedure:

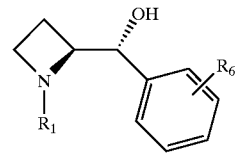

3

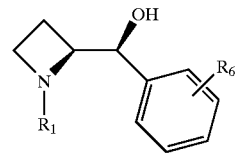

4 wherein $R_1$ and $R_6$ are as defined in the table:

| Prep. | $R_1$ | $R_6$ | Analytical Data |
|---|---|---|---|
| 3b | PhCH₂ | 3-CF₃ | MS calcd for $C_{18}H_{18}F_3NO.H^+$ m/z=322.14 observed m/z=322(M+1)⁺ |
| 3c | CH₂=CHCH₂ | 3-CF₃ | MS calcd for $C_{14}H_{16}F_3NO.H^+$ m/z=272.13 observed m/z=272(M+1)⁺ |
| 3d | CH₂=CHCH₂ | 3-Cl | MS calcd for $C_{13}H_{16}ClNO.H^+$ m/z=238.10 observed m/z=238(M+1)⁺ |
| 3e | Ph₂CH | 3-CF₃ | MS calcd for $C_{24}H_{22}F_3NO.H^+$ m/z=398.17 observed m/z=398.2(M+1)⁺ |
| 3f | Ph₂CH | 3-OCH₃ | MS calcd for $C_{24}H_{25}NO_2.H^+$ m/z=360.20 observed m/z=360.3(M+1)⁺ |
| 3g | Ph₂CH | 3-CH₃ | MS calcd for $C_{24}H_{25}NO.H^+$ m/z=344.20 observed m/z=344(M+1)⁺ |
| 3h | Ph₂CH | 4-OCH₃ | MS calcd for $C_{24}H_{25}NO_2.H^+$ m/z=360.20 observed m/z=360(M+1)⁺ |
| 3i | Ph₂CH | 3-NH₂ | MS calcd for $C_{23}H_{24}N_2O.H^+$ m/z=345.20 observed m/z=345(M+1)⁺ |
| 3j | Ph₂CH | 3-F | MS calcd for $C_{23}H_{22}FNO.H^+$ m/z=348.18 observed m/z=348(M+1)⁺ |
| 3k | Ph₂CH | 3-F-4-CH₃ | MS calcd for $C_{24}H_{24}FNO.H^+$ m/z=362.19 observed m/z=362.1(M+1)⁺ |
| 3l | Ph₂CH | 3,5-F₂ | MS calcd for $C_{23}H_{21}F_2NO.H^+$ m/z=366.17 observed m/z=366(M+1)⁺ |
| 3m | Ph₂CH | 4-CH₃ | ¹H NMR(400MHz, CDCl₃)δ 7.51(d, 2H, J=10), 7.47(d, 2H, J=9), 7.34–7.42(m, 4H), 7.25–7.41(m, 2H), 7.08(d, 2H, J=9), 7.00 (d, 2H, J=9), 4.60(s, 1H, CHPh₂), 3.87(s, 1H), 3.51(m, 1H), 3.37–3.44(m, 2H), 2.77–2.84(m, 1H), 2.32(s, 3H, Me), 2.20–2.31 (m, 1H), 1.04–1.12(m, 1H) |
| 3n | Ph₂CH | 4-Cl | ¹H NMR(400MHz, CDCl₃)δ 7.51(d, 2H, J=8), 7.47(d, 2H, J=8), 7.34–7.40(m, 4H), 7.28–7.31(m, 2H), 7.25(d, 2H, J=8), 7.07 (d, 2H, J=8), 4.61(s, 1H, CHPh₂), 3.96(br s, 1H), 3.58(dt, 1H, J=3,8), 3.40–3.43(m, 2H), 2.82(q, 1H, J=9), 2.09–2.21(m, 1H), 1.52(dq, 1H, J=3,8) |
| 3o | PhCH₂ | 4-PhO | ¹H NMR(400MHz, CDCl₃)δ 7.52(d, 2H, J=8), 7.50(d, 2H, J=8), 7.28–7.42(m, 9H), 7.09–7.16(m, 2H), 7.01(d, 2H, J=8), 6.94 (d, 2H, J=8), 4.65(s, 1H, CHPh₂), 3.92(s, 1H), 3.62(dt, 1H, J=4,8), 3.43–3.47(m, 2H), 2.85(q, 1H, J=4), 2.28–2.34(m, 1H) |

-continued

| Prep. | R₁ | R₆ | Analytical Data |
|---|---|---|---|
| 3p | Ph₂CH | 2-CH₃ | $^1$H NMR(400MHz, CDCl₃)δ 7.50–7.53(m, 4H), 7.30–7.42(m, 4H), 7.10–7.20(m, 4H), 7.02(d, 2H, J=8), 4.61(s, 1H, CHPh₂), 4.00 (s, 1H), 3.76(d, 1H, J=3), 3.63(m, 1H), 3.45(m, 1H), 2.81(m, 1H), 2.36(m, 1H), 1.85(s, 3H), 1.52–1.57(m, 1H) |
| 4b | PhCH₂ | 3-CF₃ | MS calcd for C₁₈H₁₈F₃NO.H⁺ m/z=322.14 observed m/z=322(M+1)⁺ |
| 4c | CH₂=CHCH₂ | 3-CF₃ | MS calcd for C₁₄H₁₆F₃NO.H⁺ m/z=272.13 observed m/z=272(M+1)⁺ |
| 4d | CH₂=CHCH₂ | 3-Cl | MS calcd for C₁₃H₁₆ClNO.H⁺ m/z=238.10 observed m/z=238(M+1)⁺ |
| 4e | Ph₂CH | 3-CF₃ | MS calcd for C₂₄H₂₂F₃NO.H⁺ m/z=398.17 observed m/z=398.2(M+1)⁺ |
| 4f | Ph₂CH | 3-OCH₃ | $^1$H NMR(400MHz, CDCl₃)δ 7.45(d, 2H, J=9Hz, ArH)7.20–7.38(m, 9H, ArH)6.86 (d, 1H, J=9Hz, ArH)6.78–6.82(m, 2H, ArH)4.56(br s, 1H)4.51(d, 1H, J=4Hz) 3.82(s, 3H, OCH3)3.65(q, 1H, J=7Hz) 3.30–3.38(m, 1H)2.84(q, 1H, J=7Hz) 2.34(Br s, 1H)2.00(qu, 1H, J=7Hz)1.78–1.88 (m, 1H) |
| 4g | Ph₂CH | 3-CH₃ | $^1$H NMR(400MHz, CDCl₃)δ 7.45(d, 2H, J=9Hz, ArH)7.18–7.38(m, 9H, ArH)7.15 (d, 1H, J=9Hz, ArH)6.98–7.03(m, 2H, ArH)4.98(br s, 1H)4.45(d, 1H, J=5Hz) 3.56(q, 1H, 5Hz)3.28(m, 1H)2.78(q, 1H, 6Hz)2.30(s, 3H, CH₃)1.86–1.97(m, 1H) 1.68–1.78(m, 1H) |
| 4h | Ph₂CH | 4-OCH₃ | — |
| 4j | Ph₂CH | 3-F | $^1$H NMR(400MHz, CDCl₃)δ 7.38(d, 2H, J=9Hz, ArH)7.15–7.32(m, 9H, ArH)6.95 (d, 1H, J=9Hz, ArH)6.82–6.89(m, 2H, ArH)4.48(br s, 1H)4.42–4.46(m, 1H)3.58 (q, 1H, J=5Hz)3.30–3.35(m, 1H)2.80(q, 1H, J=7Hz)2.58(br s, 1H)1.92–2.05(m, 1H)1.78–1.86(m, 1H) |
| 4k | Ph₂CH | 3-F-4-CH₃ | — |
| 4l | Ph₂CH | 3,5-F₂ | $^1$H NMR(400MHz, CDCl₃)δ 7.12–7.35(m, 10H, ArH)6.53–6.66(m, 3H, ArH)4.48(br s, 1H)4.35(br s, 1H)3.60–3.67(m, 1H) 3.30–3.40(m, 1H)2.80–2.89(m, 1H)2.65 (br s, 1H)1.90–2.08(m, 2H) |
| 4m | Ph₂CH | 4-CH₃ | $^1$H NMR(400MHz, CDCl₃)δ 7.50(d, 2H, J=10, ArH), 7.23–7.38(m, 8H), 7.14(d, 2H, J=9, ArH), 7.10(d, 2H, J=9, ArH), 4.47–4.62 (br m, 2H), 3.52–3.63(br m, 1H), 3.23–3.37 (br m, 1H), 2.73–2.86(br m, 1H), 2.33(s, 3H, Me), 1.89–2.00(m, 2H), 1.71–1.82(m, 1H) |
| 4o | PhCH₂ | 4-PhO | $^1$H NMR(400MHz, CDCl₃)δ 7.54(d, 2H, J=8), 7.28–7.36(m, 9H), 7.18(d, 2H, J=8), 7.04–7.10(m, 2H), 6.96(d, 2H, J=8), 6.88 (d, 2H, J=8), 4.52(s, 1H, CHPh₂), 4.45 (d, 1H, J=8), 3.55(q, 1H, J=4), 3.24–3.34 (m, 1H), 2.78(q, 1h, J=4), 1.85–1.97(m, 1H), 1.71–1.79(m, 1H) |

The following compounds were also prepared by an analogous procedure:

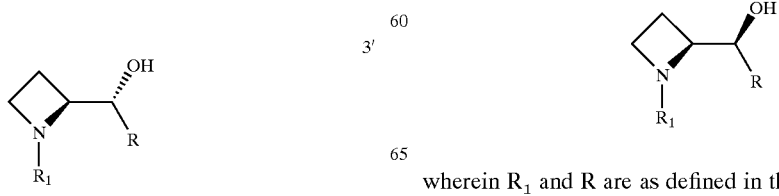

wherein R₁ and R are as defined in the table (wherein Ph is phenyl):

| Prep. | R₁ | R | Analytical Data |
|---|---|---|---|
| 3q | Ph$_2$CH | PhCH$_2$ | MS calcd for C$_{24}$H$_{25}$NO.H$^+$ m/z=344.2 observed m/z=344(M+1)$^+$ |
| 3r | Ph$_2$CH | 4-BnO-PhCH$_2$ | $^1$H NMR(400MHz, CDCl$_3$)δ 7.14–7.48(m, 17H), 6.86(d, 2H, J=8), 4.99(t, 2H, J=4), 4.52(s, 1H, CHPh$_2$), 3.92(s, 1H), 3.66(s, 1H), 3.52(dt, 1H, J=4, 8), 3.33(dt, 1H, J=4, 8), 2.71(q, 1H0 J=4), 2.21(m, 1H), 1.72(s, 2H), 1.39(q, 1H, J=4) |
| 4s | Ph$_2$CH | 2-thiazolyl | MS calcd for C$_{20}$H$_{20}$N$_2$OS.H$^+$ m/z=337.14 observed m/z=337(M+1)$^+$ |
| 3ac + 4ac (mix) | Ph$_2$CH | 3, 5-Cl$_2$—C$_6$H$_3$CH$_2$ | — |

Step D:

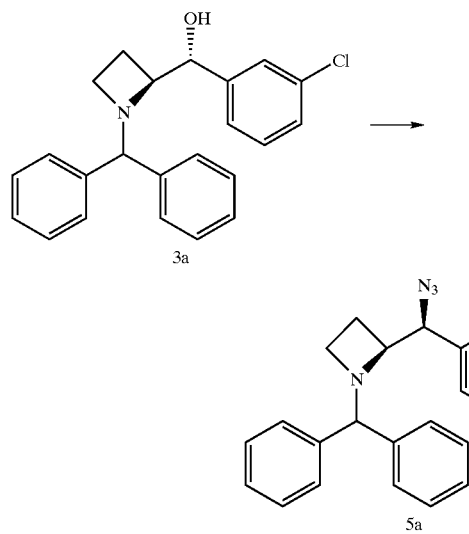

To an argon degassed solution of erythro alcohol 3a (2.00 g, 5.50 mmol) and triphenylphosphine (2.89 g, 11.0 mmol) in toluene (27 ml) was added Zn(N$_3$)$_2$.2Pyr complex (1.27 g, 4.13 mmol). To the resulting suspension at RT was added diisopropylazodicarboxylate (2.20 ml, 11.0 mmol) dropwise over 25 min. A slight exotherm was noted. The reaction was stirred at RT for 1.5 h, filtered through Celite, and concentrated in vacuo to give 8.23 g of a foamy residue. The residue was purified by chromatography over 450 g SiO$_2$. The erythro and threo azides were eluted with a gradient starting with 0.5% EtOAc in hexanes and progressing to 6% EtOAc in hexanes to give two main fractions. Fraction 1 contained 0.96 g of a mixture of the erythro and threo azides, 6a and 5a respectively. Fraction 2 contained 0.51 g of the more polar threo azide, 5a.

Analytical data for 5a: MS calcd for C$_{23}$H$_{21}$ClN$_4$.H$^+$ m/z=389.15, observed m/z=389.15 (M+1)$^+$.

The following compounds were prepared by an analogous procedure:

| Prep. | R$_1$ | R$_6$ | Analytical Data |
|---|---|---|---|
| 5b | PhCH$_2$ | 3-CF$_3$ | MS calcd for C$_{18}$H$_{17}$F$_3$N$_4$.H$^+$ m/z=347.15 observed m/z=347 (M+1)$^+$ |
| 5c | CH$_2$=CHCH$_2$ | 3-CF$_3$ | MS calcd for C$_{14}$H$_{15}$F$_3$N$_4$.H$^+$ m/z=297.13 observed m/z=297 (M+1)$^+$ |
| 5d | CH$_2$=CHCH$_2$ | 3-Cl | MS calcd for C$_{13}$H$_{15}$ClN$_4$.H$^+$ m/z=263.11 observed m/z=263 (M+1)$^+$ |
| 5e | Ph$_2$CH | 3-CF$_3$ | $^1$H NMR(400MHz, CDCl$_3$)δ 7.20–7.63(m, 14H), 4.62(s, 1H), 3.73(m, 2H), 3.09(m, 1H), 2.70 (q, 1H), 1.82(m, 1H), 1.53(m, 1H) |
| 5f | Ph$_2$CH | 3-OCH$_3$ | MS calcd for C$_{24}$H$_{24}$N$_4$O.H$^+$ m/z=385.20 observed m/z=385.1(M+1)$^+$ |
| 5g | Ph$_2$CH | 3-CH$_3$ | $^1$H NMR(400MHz, CDCl$_3$)δ 7.08–7.46(m, 14H), 4.88(s, 1H), 3.87(m, 1H), 3.54(d, 1H), 3.17 (m, 1H), 2.59(q, 1H), 2.38(s, 3H) 2.33(m, 1H), 1.81(m, 1H) |
| 5h | Ph$_2$CH | 4-OCH$_3$ | $^1$H NMR(400MHz, CDCl$_3$)δ 7.14–7.50(m, 12H), 6.88(d, 2H), 4.18(s, 1H), 3.89(d, 1H), 3.83 (s, 3H), 3.58(m, 1H), 3.13(m, 1H), 2.68(m, 1H), 1.66(m, 2H) |
| 5j | Ph$_2$CH | 3-F | $^1$H NMR(400MHz, CDCl$_3$)δ 7.19–7.48(m, 11H), 7.12(m, 3H), 4.63(s, 1H), 3.78(d, 1H), 3.64 (m, 1H), 3.13(m, 1H), 2.69(q, 1H), 1.77(m, 1H), 1.60(m, 1H) |
| 5k | Ph$_2$CH | 3-F-4-CH$_3$ | $^1$H NMR(400MHz, CDCl$_3$)δ 7.12–7.53(m, 11H), 6.95(d, 2H), 4.64(s, 1H), 3.78(d, 1H), 3.60 (m, 1H), 3.14(m, 1H), 2.69(q, 1H), 2.28(s, 3H), 1.75(m, 1H), 1.63(m, 1H) |
| 5l | Ph$_2$CH | 3,5-F$_2$ | $^1$H NMR(400MHz, CDCl$_3$)δ 7.20–7.48(m, 10H), 6.88(d, 2H), 6.76(t, 1H), 4.60(s, 1H), 3.65 (m, 2H), 3.15(m, 1H), 2.70(q, 1H), 1.83(m, 1H), 1.57(m, 1H) |
| 5m | Ph$_2$CH | 4-CH$_3$ | MS calcd for C$_{24}$H$_{24}$N$_4$.H$^+$ m/z=369.21 observed m/z=369.2(M+1)$^+$ |
| 5n | Ph$_2$CH | 4-Cl | MS calcd for C$_{23}$H$_{21}$ClN$_4$.H$^+$ m/z=389.15 observed m/z=389(M+1)$^+$ |
| 5o | Ph$_2$CH | 4-PhO | $^1$H NMR(400MHz, CDCl$_3$)δ 7.20–7.44(m, 4H), 7.19–7.35(m, 9H), 7.11(t, 2H, J=8), 7.01 (d, 2H, J=8), 6.98(d, 2H, J=8), 4.65(s, 1H, CHPh$_2$), 3.87(d, 1H, J=8), 3.62(q, 1H, J=4), 3.12–3.20(m, 1H), 3.07(q, 1H, J=4), 1.62–1.80 (m, 2H) |
| 5p | Ph$_2$CH | 2-CH$_3$ | $^1$H NMR(400MHz, CDCl$_3$)δ 7.53(d, 2H, J=7), 7.36–7.40(m, 6H), 7.25–7.31(m, 2H), 7.18–7.23 (m, 4H), 4.84(s, 1H, CHPh$_2$), 4.66 (d, 1H, J=7), 3.70(q, 1H, J=8), 3.26(m, 1H), 2.78(q, 1H, J=7), 2.46(s, 3H), 1.72(m, 2H) |

-continued

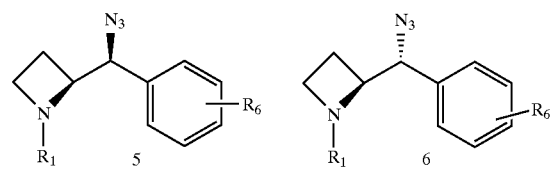

| Prep. | R₁ | R₆ | Analytical Data |
|---|---|---|---|
| 6b | PhCH₂ | 3-CF₃ | MS calcd for $C_{18}H_{17}F_3N_4.H^+$ m/z=347.15 observed m/z= 347(M+1)⁺ |
| 6c | CH₂=CHCH₂ | 3-CF₃ | MS calcd for $C_{14}H_{15}F_3N_4.H^+$ m/z=297.13 observed m/z= 297(M+1)⁺ |
| 6i | Ph₂CH | 3-NH₂ | ¹H NMR(400MHz, CDCl₃)δ 7.11–7.46(m, 11H), 6.86(d, 1H), 6.76(s, 1H), 6.65(d, 1H), 4.96(s, 1H), 3.86(m, 1H), 3.72(br s, 2H), 3.48(d, 1H), 3.17(m, 1H), 2.51 (m, 1H), 2.34(m, 1H), 1.79(m, 1H) |
| 6k | Ph₂CH | 3-F-4-CH₃ | MS calcd for $C_{24}H_{23}FN_4.H^+$ m/z=387.20 observed m/z=387 (M+1)⁺ |
| 6m | Ph₂CH | 4-CH₃ | MS calcd for $C_{24}H_{24}N_4.H^+$ m/z=369.21 observed m/z= 369.2(M+1)⁺ |

The following compounds were also prepared by an analogous procedure:

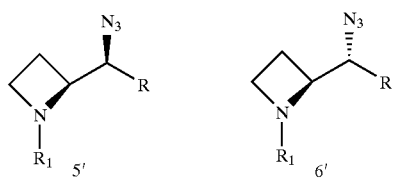

| Ex. | R₁ | R | Analytical Data |
|---|---|---|---|
| 5q | Ph₂CH | PhCH₂ | ¹H NMR(400MHz, CDCl₃)δ 7.04–7.52 (m, 15H), 4.78(s, 1H), 4.60(d, 1H, J=10), 3.64(q, 1H, J=9), 3.21(m, 1H), 2.73(q, 1H, J=8), 2.20(s, 2H), 1.66(m, 2H) |
| 5r | Ph₂CH | 4-BnOPhCH₂ | MS calcd for $H_{31}H_{30}N_4O.H^+$ m/z= 475.25 observed m/z=475(M+1)⁺ |
| 5s | Ph₂CH | 2-thiazolyl | ¹H NMR(400MHz, CDCl₃)δ 7.15–7.70 m, 12H), 4.54(s, 1H), 4.10(m, 1H), 3.75(d, 1H, J=3), 3.48(m, 1H), 2.78(q, 1H, J=8), 2.28(m, 1H), 1.78(m, 1H) |

Step E:

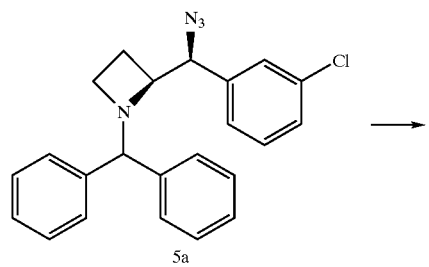

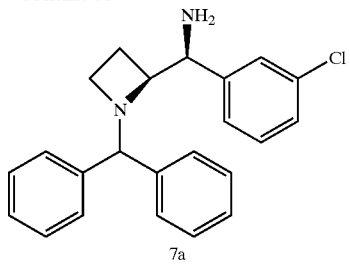

To a solution of the threo azide 5a (0.50 g, 1.29 mmol) in CH₃OH (10 ml) at 0° C. was added NiCl₂.6H₂O (1.47 g, 6.19 mmol). To this solution was added NaBH₄ (0.39 g, 10.3 mmol) in portions. The reaction was stirred at 0° C. for 1.5 h, then quenched with the dropwise addition of 3.4 ml water. It was partitioned between water (40 ml) and EtOAc (100 ml). The aqueous layer was extracted with EtOAc (2×100 ml). The combined EtOAc layers were washed with brine (50 ml), dried over anhydrous Na₂SO₄ and concentrated in vacuo to give 0.473 g of an oil. The oil was purified by column chromatography over 100 g SiO₂, eluting with a solvent gradient starting with 0.5% CH₃OH in CH₂Cl₂ and progressing to 3% CH₃OH in CH₂Cl₂. Concentration of the appropriate fractions gave 0.31 g of the desired racemic threo amine 7a as an oil. The enantiomers were separated by preparative HPLC on a Chiracel OJ column eluting with 5% EtOH in hexanes containing 0.2% Et₂NH.

Analytical data for racemic 7a:
MS calcd for $C_{23}H_{23}ClN_2.H^+$ m/z=363.16, observed m/z= 363.10 (M+1)⁺.

Analytical data for the first eluted enantiomer 7a-E1:
MS calcd for $C_{23}H_{23}ClN_2.H^+$ m/z=363.16, observed m/z= 363.30 (M+1)⁺.

Analytical data for the second eluted enantiomer 7a-E2:
MS calcd for $C_{23}H_{23}ClN_2.H^+$ m/z=363.16, observed m/z= 363.30 (M+1)⁺.

The following compounds were prepared by an analogous procedure:

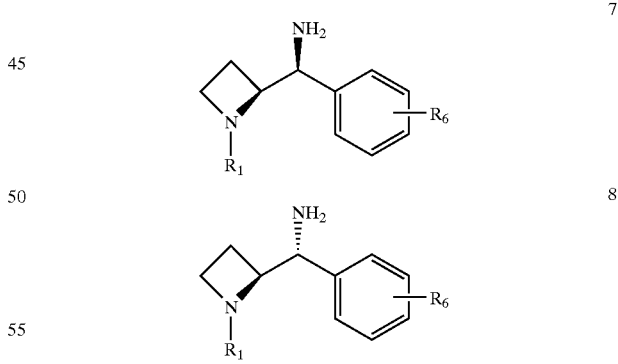

wherein R₁ and R₆ are defined in the table:

| Prep. | R₁ | R₆ | Analytical Data |
|---|---|---|---|
| 7b | PhCH₂ | 3-CF₃ | MS calcd for $C_{18}H_{19}F_3N_2.H^+$ m/z=321.16 observed m/z=321(M+1)⁺ |
| 7c | CH₂=CHCH₂ | 3-CF₃ | MS calcd for $C_{14}H_{17}F_3N_2.H^+$ m/z=271.14 observed m/z=271(M+1)⁺ |

-continued

| Prep. | R₁ | R₆ | Analytical Data |
|---|---|---|---|
| 7d | CH₂=CHCH₂ | 3-Cl | MS calcd for $C_{13}H_{17}ClN_2.H^+$ m/z=237.12 observed m/z=237.1(M+1)⁺ |
| 7e | Ph₂CH | 3-CF₃ | MS calcd for $C_{24}H_{23}F_3N_2.H^+$ m/z=397.19 observed m/z=397.4(M+1)⁺ |
| 7e-E1 | Ph₂CH | 3-CF₃ | MS calcd for $C_{24}H_{23}F_3N_2.H^+$ m/z=397.19 observed m/z=397.4(M+1)⁺ |
| 7e-E2 | Ph₂CH | 3-CF₃ | MS calcd for $C_{24}H_{23}F_3N_2.H^+$ m/z=397.19 observed m/z=397.4(M+1)⁺ |
| 7f | Ph₂CH | 3-OCH₃ | MS calcd for $C_{24}H_{26}N_2O.H^+$ m/z=359.21 observed m/z=359.1(M+1)⁺ |
| 7g | Ph₂CH | 3-CH₃ | MS calcd for $C_{24}H_{26}N_2.H^+$ m/z=343.22 observed m/z=343(M+1)⁺ |
| 7h | Ph₂CH | 4-OCH₃ | MS calcd for $C_{24}H_{26}N_2O.H^+$ m/z=359.21 observed m/z=359.1(M+1)⁺ |
| 7j | Ph₂CH | 3-F | MS calcd for $C_{23}H_{23}FN_2.H^+$ m/z=347.19 observed m/z=347(M+1)⁺ |
| 7k | Ph₂CH | 3-F-4-CH₃ | MS calcd for $C_{24}H_{25}FN_2.H^+$ m/z=361.21 observed m/z=361.1(M+1)⁺ |
| 7l | Ph₂CH | 3,5-F₂ | MS calcd for $C_{23}H_{22}F_2N_2.H^+$ m/z=365.19 observed m/z=365.1(M+1)⁺ |
| 7m | Ph₂CH | 4-CH₃ | MS calcd for $C_{24}H_{26}N_2.H^+$ m/z=343.22 observed m/z=343.4(M+1)⁺ |
| 7n | Ph₂CH | 4-Cl | MS calcd for $C_{23}H_{23}ClN_2.H^+$ m/z=363.16 observed m/z=363(M+1)⁺ |
| 7n-E1 | Ph₂CH | 4-Cl | MS calcd for $C_{23}H_{23}ClN_2.H^+$ m/z=363.16 observed m/z=363(M+1)⁺ |
| 7n-E2 | Ph₂CH | 4-Cl | MS calcd for $C_{23}H_{23}ClN_2.H^+$ m/z=363.16 observed m/z=363(M+1)⁺ |
| 7o | Ph₂CH | 4-PhO | MS calcd for $C_{29}H_{28}N_2O.H^+$ m/z=421.23 observed m/z=421(M+1)⁺ |
| 7p | Ph₂CH | 2-CH₃ | MS calcd for $C_{24}H_{26}N_2.H^+$ m/z=343.22 observed m/z=343(M+1)⁺ |
| 8b | PhCH₂ | 3-CF₃ | MS calcd for $C_{18}H_{19}F_3N_2.H^+$ m/z=321.16 observed m/z=321(M+1)⁺ |
| 8c | CH₂=CHCH₂ | 3-CF₃ | MS calcd for $C_{14}H_{17}F_3N_2.H^+$ m/z=271.14 observed m/z=271(M+1)⁺ |
| 8i | Ph₂CH | 3-NH₂ | MS calcd for $C_{23}H_{25}N_3.H^+$ m/z=344.21 observed m/z=344.1(M+1)⁺ |
| 8k | Ph₂CH | 3-F-4-CH₃ | MS calcd for $C_{24}H_{25}FN_2.H^+$ m/z=361.21 observed m/z=361.1(M+1)⁺ |

The following compounds were also prepared by an analogous procedure:

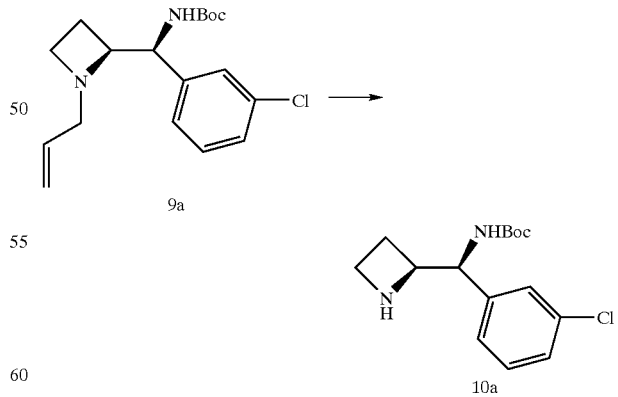

| Ex. | R₁ | R | Analytical Data |
|---|---|---|---|
| 7q | Ph₂CH | PhCH₂ | MS calcd for $C_{24}H_{26}N_2.H^+$ m/z=343.22 observed m/z=343(M+1)⁺ |
| 7q-E1 | Ph₂CH | PhCH₂ | MS calcd for $C_{24}H_{26}N_2.H^+$ m/z=343.22 observed m/z=343.4(M+1)⁺ |
| 7q-E2 | Ph₂CH | PhCH₂ | MS calcd for $C_{24}H_{26}N_2.H^+$ m/z=343.22 observed m/z=343.4(M+1)⁺ |
| 7r | Ph₂CH | 4-BnOPhCH₂ | MS calcd for $C_{31}H_{32}N_2O.H^+$ m/z=449.26 observed m/z=449.3(M+1)⁺ |
| 7s | Ph₂CH | 2-thiazolyl | MS calcd for $C_{20}H_{21}N_3S.H^+$ m/z=336.15 observed m/z=336.1(M+1)⁺ |

Step F:

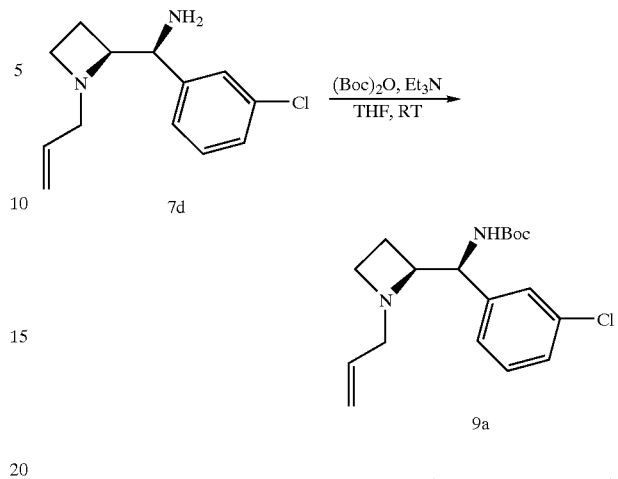

To a stirred solution of compound 7d (3.41 g, 14.4 mmol) and Et₃N (1.6 g, 16 mmol) in THF (40 ml) was added a solution of di-tert-butyl dicarbonate (3.52 g, 16 mmol) in THF (20 ml) over 1 h. The mixture was stirred at RT for another 2 h and then concentrated. The residue was chromatographed over silica gel, eluting with a solvent gradient starting with 5% EtOAc in hexanes progressing to 20% EtOAc in hexanes to give 3.69 g (76%) of product 9a as a colorless oil. MS calcd for $C_{18}H_{25}ClN_2O_2.H^+$ m/z=337.17, observed m/z=337 (M+1)⁺.

The following compound was prepared by an analogous procedure:

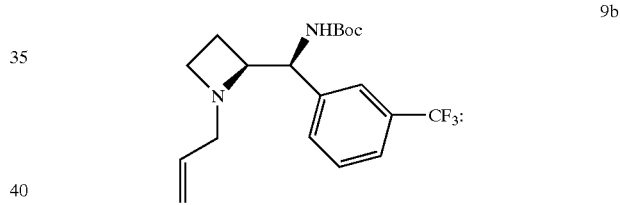

MS calcd for $C_{19}H_{25}F_3N_2O_2.H^+$ m/z=371.19, observed m/z=371 (M+1)⁺.

Step G:

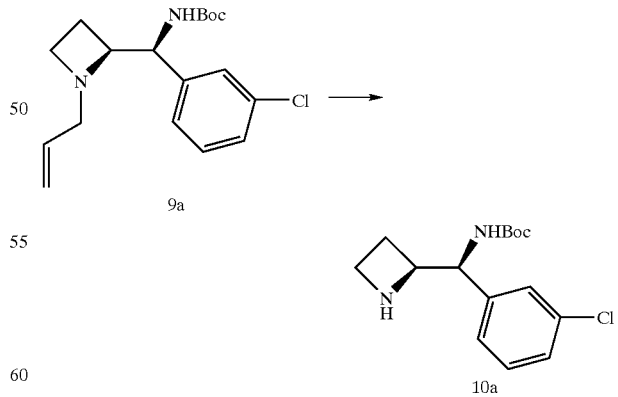

A suspension of Pd₂(dba)₃ (275 mg, 0.3 mmol) and DPPB (256 mg, 0.6 mmol) in THF (3 ml) under N₂ was stirred at RT for 30 min. The above catalyst was added slowly to a stirred solution of compound 9a and thiosalicylic acid in THF (35 ml). The mixture was stirred at RT for another 2 h and then concentrated in vacuo. The residue was chromatographed over silica gel, eluting with a solvent gradient starting with 20% EtOAc in hexanes progressing to 66% EtOAc in hexanes containing 1% CH$_3$OH to give 1.15 g (73%) of product 10a as a pale yellow solid and 0.15 g of starting material 9a (8%). MS calcd for C$_{15}$H$_{21}$ClN$_2$O$_2$.H$^+$ m/z=297.14, observed m/z=297 (M+1)$^+$.

The following compound was prepared by an analogous procedure:

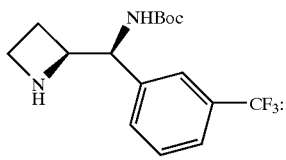

10b

MS calcd for C$_{16}$H$_{21}$F$_3$N$_2$O$_2$.H$^+$ m/z=331.16, observed m/z=331 (M+1)$^+$.

Step H:
  See Example 1.
Step I:
  See Example 2.
Step J:
  See Example 3.
Step K:

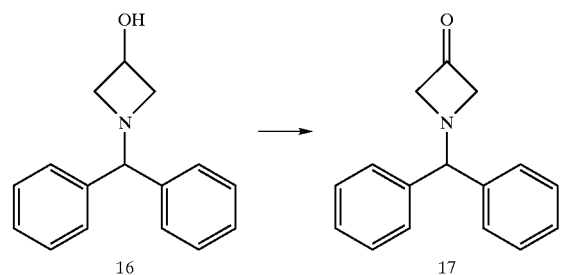

To 1-diphenylmethyl-3-hydroxyazetidine (2.00 g, 7.26 mmol), 16, in CH$_2$Cl$_2$ (35 ml) was added diisopropylethylamine (7.6 ml, 44 mmol). The solution was cooled to 0° C. and sulfurtrioxide-pyridine (3.47 g, 21.8 mmol) in DMSO (6 ml) was slowly added. The solution was stirred overnight while the cold bath expired. The solution was partitioned between Et$_2$O (100 ml) and brine (50 ml). The aqueous layer was extracted with Et$_2$O (2×50 ml). The combined Et$_2$O layers were washed with half-saturated brine (100 ml), dried over Na$_2$SO$_4$, and concentrated in vacuo. The residue was chromatographed over 60 g SiO$_2$, eluting with a solvent gradient starting with 2% EtOAc in hexanes, progressing to 10% EtOAc in hexanes. Concentration of the appropriate fractions yielded 1.24 g (72%) of the desired ketone, 17, as a white solid:

EXAMPLE 1

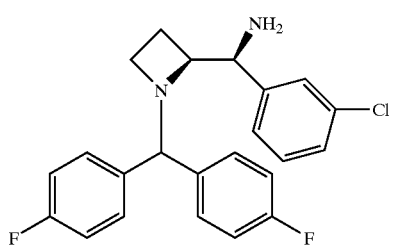

Ex. 1a

A suspension of compound 10a (20 mg, 0.067 mmol), 4,4'-difluorobenzhydryl chloride (50 mg, 0.21 mmol), NaI (10 mg, 0.067 mmol) and Et$_3$N (20 mg, 0.2 mmol) in CH$_3$CN (2 ml) was stirred at 50° C. for 14 h. The solvent was removed in vacuo, the residue was suspended in TFA (2 ml) and CH$_2$Cl$_2$ (2 ml). The mixture was stirred at RT for 2 h and concentrated. The residue was purified by preparative TLC, eluting with 33% EtOAc in hexanes containing 1% CH$_3$OH to give 12.4 mg (46% in two steps) of product 1a, which was treated with HCl in ether to generate the dihydrochloric acid salt. MS calcd for C$_{23}$H$_{21}$ClF$_2$N$_2$.H$^+$ m/z=399.14, observed m/z=399 (M+1)$^+$.

Enantiomers were resolved using chiral chromatography over either Chiralcel OD or OJ columns on either the free amine or their N-Boc derivatives and appear in the tables with the notations, E1 or E2.

The following compounds were prepared by an analogous procedure:

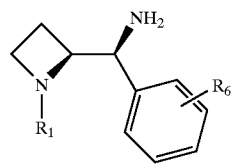

| Ex. | R$_1$ | R$_6$ | Analytical Data |
|---|---|---|---|
| 1b | 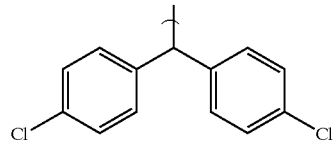 | 3-Cl | MS calcd for C$_{23}$H$_{21}$Cl$_3$N$_2$.H$^+$ m/z=431.08 observed m/z=431(M+1)$^+$ |

-continued

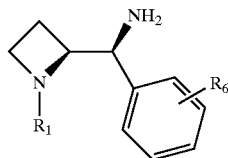

| Ex. | R$_1$ | R$_6$ | Analytical Data |
|---|---|---|---|
| 1c | 4-Br-C$_6$H$_4$–CH–C$_6$H$_4$-4-Br | 3-Cl | MS calcd for C$_{23}$H$_{21}$Br$_2$ClN$_2$.H$^+$ m/z=518.98 observed m/z=519.0, 520.9, 521.9(M+1)$^+$ |
| 1d | 4-Me-C$_6$H$_4$–CH–C$_6$H$_4$-4-Me | 3-Cl | MS calcd for C$_{25}$H$_{27}$ClN$_2$.H$^+$ m/z=391.19 observed m/z=391(M+1)$^+$ |
| 1e | 3-F-C$_6$H$_4$–CH–C$_6$H$_4$-3-F | 3-Cl | MS calcd for C$_{23}$H$_{21}$ClF$_2$N$_2$.H$^+$ m/z=399.14 observed m/z=399(M+1)$^+$ |
| 1f | 3-Cl-C$_6$H$_4$–CH–C$_6$H$_4$-3-Cl | 3-Cl | MS calcd for C$_{23}$H$_{21}$Cl$_3$N$_2$.H$^+$ m/z=431.08 observed m/z=431(M+1)$^+$ |
| 1g | 3-CF$_3$-C$_6$H$_4$–CH–C$_6$H$_4$-3-CF$_3$ | 3-Cl | MS calcd for C$_{25}$H$_{21}$ClF$_6$N$_2$.H$^+$ m/z=499.14 observed m/z=499(M+1)$^+$ |
| 1h | 2-pyridyl–CH–Ph | 3-Cl | MS calcd for C$_{22}$H$_{22}$ClN$_3$.H$^+$ m/z=364.16 observed m/z=364(M+1)$^+$ |
| 1h diast. 1-E1 | 2-pyridyl–CH–Ph | 3-Cl | MS calcd for C$_{22}$H$_{22}$ClN$_3$.H$^+$ m/z=364.16 observed m/z=364(M+1)$^+$ |
| 1h diast. 1-E2 | 2-pyridyl–CH–Ph | 3-Cl | MS calcd for C$_{22}$H$_{22}$ClN$_3$.H$^+$ m/z=364.16 observed m/z=364(M+1)$^+$ |
| 1i diast. 2 | Ph–CH–2-pyridyl | 3-Cl | MS calcd for C$_{22}$H$_{22}$ClN$_3$.H$^+$ m/z=364.16 observed m/z=364(M+1)$^+$ |

-continued

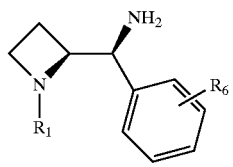

| Ex. | R$_1$ | R$_6$ | Analytical Data |
|---|---|---|---|
| 1i diast. 2-E1 | (phenyl)(2-pyridyl)methyl | 3-Cl | MS calcd for C$_{22}$H$_{22}$ClN$_3$.H$^+$ m/z=364.16 observed m/z=364(M+1)$^+$ |
| 1i diast. 2-E2 | (phenyl)(2-pyridyl)methyl | 3-Cl | MS calcd for C$_{22}$H$_{22}$ClN$_3$.H$^+$ m/z=364.16 observed m/z=364(M+1)$^+$ |
| 1j | 9-fluorenyl | 3-Cl | MS calcd for C$_{23}$H$_{21}$ClN$_2$.H$^+$ m/z=361.15 observed m/z=361(M+1)$^+$ |
| 1k | bis(3-fluorophenyl)butyl | 3-Cl | MS calcd for C$_{26}$H$_{27}$ClF$_2$N$_2$.H$^+$ m/z=441.19 observed m/z=441(M+1)$^+$ |
| 1L | benzyl | 3-Cl | MS calcd for C$_{18}$H$_{21}$ClN$_2$.H$^+$ m/z=301.15 observed m/z=301(M+1)$^+$ |
| 1m diast. 1 | 1-phenylpropyl | 3-Cl | MS calcd for C$_{19}$H$_{23}$ClN$_2$.H$^+$ m/z=315.16 observed m/z=315(M+1)$^+$ |
| 1n diast. 2 | 1-phenylpropyl | 3-Cl | MS calcd for C$_{19}$H$_{23}$ClN$_2$.H$^+$ m/z=315.16 observed m/z=315(M+1)$^+$ |
| 1o diast. 1 | 1-phenylbutyl | 3-Cl | MS calcd for C$_{20}$H$_{25}$ClN$_2$.H$^+$ m/z=329.18 observed m/z=329(M+1)$^+$ |
| 1p diast. 2 | 1-phenylbutyl | 3-Cl | MS calcd for C$_{20}$H$_{25}$ClN$_2$.H$^+$ m/z=329.18 observed m/z=329(M+1)$^+$ |

-continued

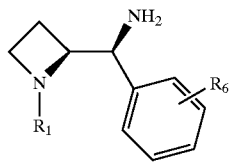

| Ex. | R₁ | R₆ | Analytical Data |
|---|---|---|---|
| 1q diast. 1 | 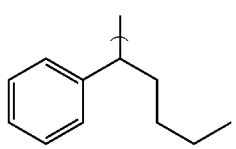 | 3-Cl | MS calcd for $C_{21}H_{27}ClN_2 \cdot H^+$ m/z=343.19 observed m/z=343(M+1)⁺ |
| 1r diast. 2 | 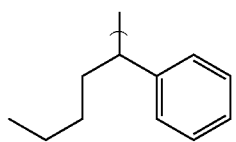 | 3-Cl | MS calcd for $C_{21}H_{27}ClN_2 \cdot H^+$ m/z=343.19 observed m/z=343(M+1)⁺ |
| 1s diast. 1 | 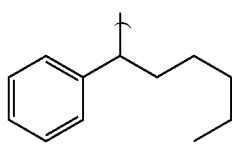 | 3-Cl | MS calcd for $C_{22}H_{29}ClN_2 \cdot H^+$ m/z=357.20 observed m/z=357(M+1)⁺ |
| 1t diast. 2 | 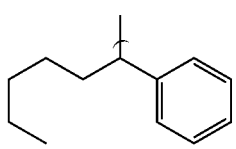 | 3-Cl | MS calcd for $C_{22}H_{29}ClN_2 \cdot H^+$ m/z=357.20 observed m/z=357(M+1)⁺ |
| 1u diast. 1 | 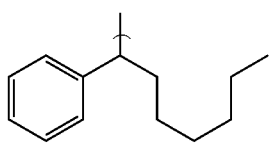 | 3-Cl | MS calcd for $C_{23}H_{31}ClN_2 \cdot H^+$ m/z=371.23 observed m/z=371(M+1)⁺ |
| 1v diast. 2 | 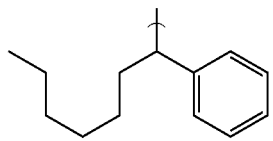 | 3-Cl | MS calcd for $C_{23}H_{31}ClN_2 \cdot H^+$ m/z=371.23 observed m/z=371(M+1)⁺ |
| 1w diast. 1 | 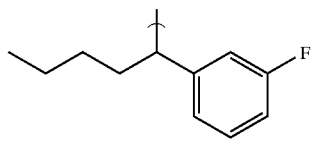 | 3-Cl | MS calcd for $C_{21}H_{26}ClFN_2 \cdot H^+$ m/z=361.18 observed m/z=361(M+1)⁺ |
| 1x diast. 2 | 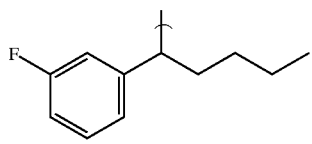 | 3-Cl | MS calcd for $C_{21}H_{26}ClFN_2 \cdot H^+$ m/z=361.18 observed m/z=361(M+1)⁺ |

-continued

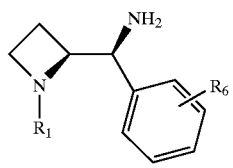

| Ex. | R₁ | R₆ | Analytical Data |
|---|---|---|---|
| 1y diast. 1 | 3,5-difluorophenyl pentyl | 3-Cl | MS calcd for $C_{21}H_{25}ClF_2N_2 \cdot H^+$ m/z=379.17 observed m/z=379(M+1)$^+$ |
| 1z diast. 2 | 3,5-difluorophenyl pentyl | 3-Cl | MS calcd for $C_{21}H_{25}ClF_2N_2 \cdot H^+$ m/z=379.17 observed m/z=379(M+1)$^+$ |
| 1aa diast. 1 | 2-pyridyl pentyl | 3-Cl | MS calcd for $C_{20}H_{26}ClN_3 \cdot H^+$ m/z=344.19 observed m/z=344(M+1)$^+$ |
| 1ab diast. 2 | 2-pyridyl pentyl | 3-Cl | MS calcd for $C_{20}H_{26}ClN_3 \cdot H^+$ m/z=344.19 observed m/z=344(M+1)$^+$ |
| 1ac | nonan-5-yl | 3-Cl | MS calcd for $C_{19}H_{31}ClN_2 \cdot H^+$ m/z=323.23 observed m/z=323(M+1)$^+$ |
| 1ad | 2-pyrimidinyl | 3-Cl | MS calcd for $C_{14}H_{15}ClN_4 \cdot H^+$ m/z=275.11 observed m/z=275(M+1)$^+$ |
| 1ae | 4-nitrobenzyl | 3-Cl | MS calcd for $C_{16}H_{16}ClN_3O_2 \cdot H^+$ m/z=318.10 observed m/z=318(M+1)$^+$ |
| 1af | 3,5-bis(trifluoromethyl)benzyl | 3-CF₃ | MS calcd for $C_{20}H_{17}F_9N_2 \cdot H^+$ m/z=457.13 observed m/z=457(M+1)$^+$ |

-continued

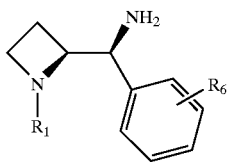

| Ex. | R₁ | R₆ | Analytical Data |
|---|---|---|---|
| 1ag | (2-biphenylmethyl) | 3-CF₃ | MS calcd for $C_{24}H_{23}F_3N_2.H^+$ m/z=397.19 observed m/z=397(M+1)⁺ |
| 1ah | (4-biphenylmethyl) | 3-CF₃ | MS calcd for $C_{24}H_{23}F_3N_2.H^+$ m/z=397.19 observed m/z=397(M+1)⁺ |
| 1ai | (3,5-dichloro-4-benzoylbenzyl) | 3-CF₃ | MS calcd for $C_{25}H_{21}Cl_2F_3N_2O.H^+$ m/z=493.11 observed m/z=493(M+1)⁺ |
| 1aj | (3-phenoxybenzyl) | 3-CF₃ | MS calcd for $C_{24}H_{23}F_3N_2O.H^+$ m/z=413.18 observed m/z=413(M+1)⁺ |
| 1ak | (benzo[1,3]dioxol-4-ylmethyl) | 3-CF₃ | MS calcd for $C_{19}H_{19}F_3N_2O_2.H^+$ m/z=365.15 observed m/z=365(M+1)⁺ |
| 1al | (9H-fluoren-9-yl) | 3-CF₃ | MS calcd for $C_{24}H_{21}F_3N_2.H^+$ m/z=395.17 observed m/z=395(M+1)⁺ |
| 1am | (phenyl(pyridin-2-yl)methyl) | 3-CF₃ | MS calcd for $C_{23}H_{22}F_3N_3.H^+$ m/z=398.18 observed m/z=398(M+1)⁺ |
| 1an | (3,3-diphenylpropyl) | 3-CF₃ | MS calcd for $C_{26}H_{27}F_3N_2.H^+$ m/z=425.22 observed m/z=425(M+1)⁺ |

-continued

| Ex. | $R_1$ | $R_6$ | Analytical Data |
|---|---|---|---|
| 1ao | 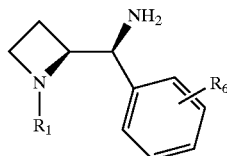 | 3-$CF_3$ | MS calcd for $C_{23}H_{22}F_3N_3.H^+$ m/z=398.18 observed m/z=398.1$(M+1)^+$ |

EXAMPLE 2

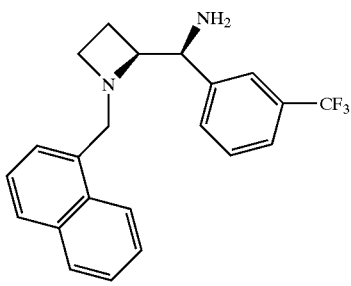

Ex. 2a

To a stirred solution of compound 10b (20 mg, 0.061 mmol), 1-naphthaldehyde (11 mg, 0.070 mmol) and acetic acid (0.06 mmol) in $CH_2Cl_2$ (1.5 ml) was added sodium triacetoxyborohydride (21 mg, 0.10 mmol). The suspension was stirred at RT for 15 h. TFA (1.5 ml) was added to the solution, and the mixture was stirred at RT for 1 h. It was concentrated and the residue was purified by preparative TLC eluting with 33% EtOAc in hexanes containing 1% $CH_3OH$ to give 9.8 mg of product (Ex. 2a). The free amine was treated with HCl in $Et_2O$ to give the dihydrochloric acid salt. MS calcd for $C_{22}H_{21}F_3N_2.H^+$ m/z=371.17, observed m/z=371 $(M+1)^+$.

The following compounds were prepared by an analogous procedure:

| Ex. | $R_1$ | $R_6$ | Analytical Data |
|---|---|---|---|
| 2b | 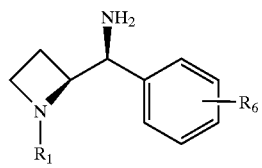 | 3-$CF_3$ | MS calcd for $C_{22}H_{21}F_3N_2.H^+$ m/z=371.17 observed m/z=371$(M+1)^+$ |
| 2c | (fluorenyl-CH2) | 3-$CF_3$ | MS calcd for $C_{25}H_{23}F_3N_2.H^+$ m/z=409.19 observed m/z=409$(M+1)^+$ |
| 2e | (4-(benzyl)piperidinyl) | 3-$CF_3$ | MS calcd for $C_{23}H_{28}F_3N_3.H^+$ m/z=404.23 observed m/z=404$(M+1)^+$ |

EXAMPLE 3

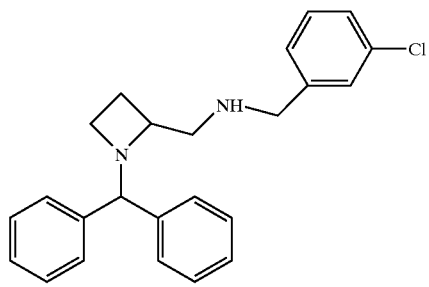
Ex. 3a

To a vial containing 2a (50 mg, 0.20 mmol) in THF (1 ml) was added 3-chlorobenzylamine (0.22 ml, 0.2mmol) as a 1M solution in 1,2-dichloroethane. The solution was stirred for 30 min, then sodium triacetoxyborohydride (42 mg, 0.20 mmol) was added. After ~2 h, the reaction was quenched with saturated $NaHCO_3$ and extracted with EtOAc. The organic layer was dried over $Na_2SO_4$, concentrated and the residue dissolved in $Et_2O$. To the ethereal solution was added ~1 ml of 1M HCl in $Et_2O$ to give the dihydrochloride salt 3a as a precipitated solid. MS calcd for $C_{24}H_{25}ClN_2.H^+$ m/z=377.18, observed m/z=377 $(M+1)^+$.

The following compounds were prepared by this reductive amination route:

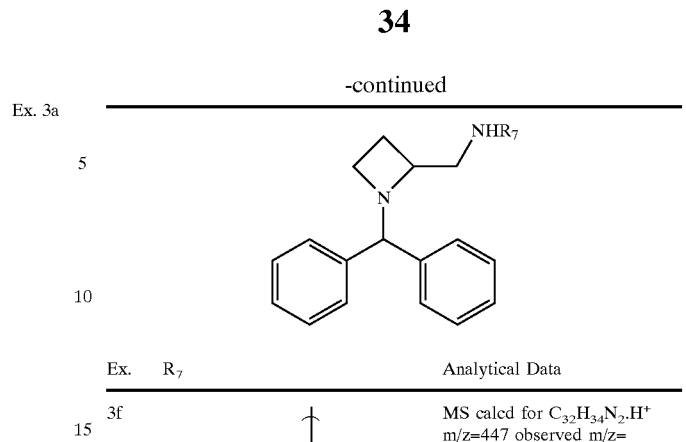

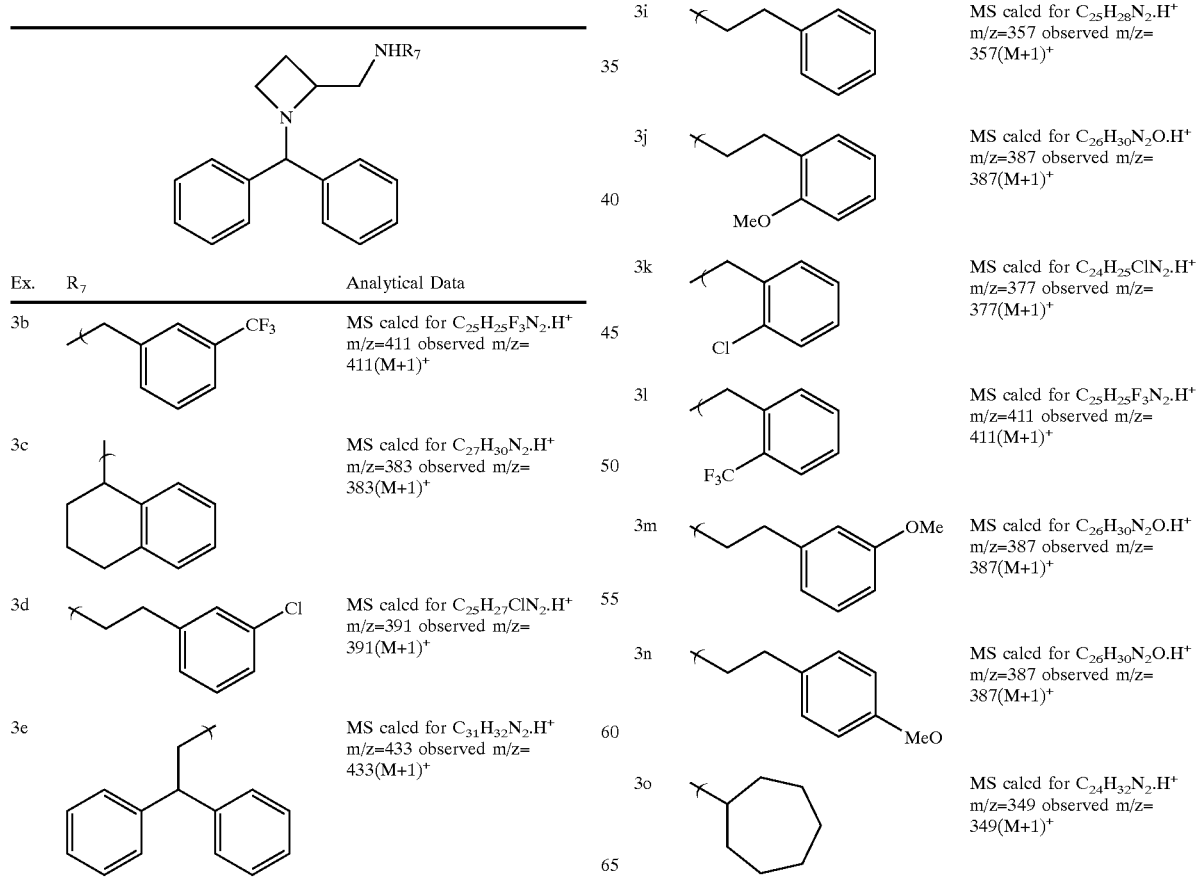

| Ex. | $R_7$ | Analytical Data |
|---|---|---|
| 3b | (3-CF$_3$-benzyl) | MS calcd for $C_{25}H_{25}F_3N_2.H^+$ m/z=411 observed m/z= 411$(M+1)^+$ |
| 3c | (tetrahydronaphthyl) | MS calcd for $C_{27}H_{30}N_2.H^+$ m/z=383 observed m/z= 383$(M+1)^+$ |
| 3d | (3-Cl-phenethyl) | MS calcd for $C_{25}H_{27}ClN_2.H^+$ m/z=391 observed m/z= 391$(M+1)^+$ |
| 3e | (diphenylmethyl-CH$_2$) | MS calcd for $C_{31}H_{32}N_2.H^+$ m/z=433 observed m/z= 433$(M+1)^+$ |
| 3f | (diphenylpropyl) | MS calcd for $C_{32}H_{34}N_2.H^+$ m/z=447 observed m/z= 447$(M+1)^+$ |
| 3g | (2-Cl-4-Me-benzyl) | MS calcd for $C_{25}H_{27}ClN_2.H^+$ m/z=391 observed m/z= 391$(M+1)^+$ |
| 3h | (2-Cl-4-F-benzyl) | MS calcd for $C_{24}H_{24}ClFN_2.H^+$ m/z=395 observed m/z= 395$(M+1)^+$ |
| 3i | (phenethyl) | MS calcd for $C_{25}H_{28}N_2.H^+$ m/z=357 observed m/z= 357$(M+1)^+$ |
| 3j | (2-MeO-phenethyl) | MS calcd for $C_{26}H_{30}N_2O.H^+$ m/z=387 observed m/z= 387$(M+1)^+$ |
| 3k | (2-Cl-benzyl) | MS calcd for $C_{24}H_{25}ClN_2.H^+$ m/z=377 observed m/z= 377$(M+1)^+$ |
| 3l | (2-CF$_3$-benzyl) | MS calcd for $C_{25}H_{25}F_3N_2.H^+$ m/z=411 observed m/z= 411$(M+1)^+$ |
| 3m | (3-MeO-phenethyl) | MS calcd for $C_{26}H_{30}N_2O.H^+$ m/z=387 observed m/z= 387$(M+1)^+$ |
| 3n | (4-MeO-phenethyl) | MS calcd for $C_{26}H_{30}N_2O.H^+$ m/z=387 observed m/z= 387$(M+1)^+$ |
| 3o | (cycloheptyl) | MS calcd for $C_{24}H_{32}N_2.H^+$ m/z=349 observed m/z= 349$(M+1)^+$ |

-continued

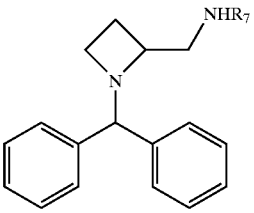

| Ex. | R₇ | Analytical Data |
|---|---|---|
| 3p | (benzyl-3-OMe) | MS calcd for $C_{25}H_{28}N_2O·H^+$ m/z=373 observed m/z=373(M+1)$^+$ |
| 3q | (phenethyl-3-Cl) | MS calcd for $C_{25}H_{27}ClN_2·H^+$ m/z=391 observed m/z=391(M+1)$^+$ |
| 3r | (benzyl-4-Cl) | MS calcd for $C_{24}H_{25}ClN_2·H^+$ m/z=377 observed m/z=377(M+1)$^+$ |
| 3s | $C_{10}H_{21}$-n | MS calcd for $C_{27}H_{40}N_2·H^+$ m/z=393 observed m/z=393(M+1)$^+$ |
| 3t | (2-pyridylethyl) | MS calcd for $C_{24}H_{27}N_3·H^+$ m/z=357 observed m/z=357(M+1)$^+$ |
| 3u | (benzyl-2,4-diCl) | MS calcd for $C_{24}H_{24}Cl_2N_2·H^+$ m/z=411 observed m/z=411, 413(M+1)$^+$ |
| 3v | (imidazolylbutyl) | MS calcd for $C_{23}H_{28}N_4·H^+$ m/z=361 observed m/z=361(M+1)$^+$ |
| 3w | Ph | MS calcd for $C_{23}H_{24}N_2·H^+$ m/z=329 observed m/z=329(M+1)$^+$ |
| 3x | (phenethyl-4-Cl) | MS calcd for $C_{25}H_{27}ClN_2·H^+$ m/z=391 observed m/z=391(M+1)$^+$ |
| 3y | (furylmethyl) | MS calcd for $C_{22}H_{24}N_2O·H^+$ m/z=333 observed m/z=333(M+1)$^+$ |
| 3z | Ph(CH₂)₄ | MS calcd for $C_{27}H_{32}N_2·H^+$ m/z=385 observed m/z=385(M+1)$^+$ |
| 3aa | (piperidinylpropyl) | MS calcd for $C_{24}H_{33}N_3·H^+$ m/z=364 observed m/z=364(M+1)$^+$ |
| 3ab | (methoxybutyl) | MS calcd for $C_{21}H_{28}N_2O·H^+$ m/z=325 observed m/z=325(M+1)$^+$ |

-continued

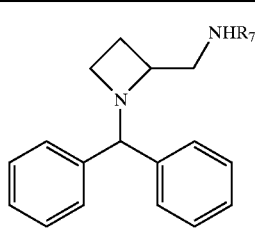

| Ex. | R₇ | Analytical Data |
|---|---|---|
| 3ac | (3-pyridylmethyl) | MS calcd for $C_{23}H_{25}N_3·H^+$ m/z=344 observed m/z=344(M+1)$^+$ |
| 3ad | (2-pyridylmethyl) | MS calcd for $C_{23}H_{25}N_3·H^+$ m/z=344 observed m/z=344(M+1)$^+$ |
| 3ae | (diphenylmethyl) | MS calcd for $C_{30}H_{30}N_2·H^+$ m/z=419 observed m/z=419(M+1)$^+$ |
| 3af | (2-oxopyrrolidinylpropyl) | MS calcd for $C_{24}H_{31}N_3O·H^+$ m/z=378 observed m/z=378(M+1)$^+$ |
| 3ag | (N-benzylpiperidinyl) | MS calcd for $C_{29}H_{35}N_3·H^+$ m/z=426 observed m/z=426(M+1)$^+$ |
| 3ah | (benzo[1,3]dioxolylmethyl) | MS calcd for $C_{25}H_{26}N_2O_2·H^+$ m/z=387 observed m/z=387(M+1)$^+$ |
| 3ai | (benzyl-4-CF₃) | MS calcd for $C_{25}H_{25}F_3N_2·H^+$ m/z=411 observed m/z=411(M+1)$^+$ |
| 3aj | (benzyl-4-OMe) | MS calcd for $C_{25}H_{28}N_2O·H^+$ m/z=373 observed m/z=373(M+1)$^+$ |
| 3ak | (4-pyridylmethyl) | MS calcd for $C_{23}H_{25}N_3·H^+$ m/z=344 observed m/z=344(M+1)$^+$ |

The following secondary amines were prepared by this reductive amination route:

| Ex. | -NR₇R₈ | Analytical Data |
|---|---|---|
| 3al | 4-benzylpiperidin-1-yl | MS calcd for $C_{29}H_{34}N_2 \cdot H^+$ m/z=411 observed m/z=411 $(M+1)^+$ |
| 3am | 4-[bis(4-fluorophenyl)methyl]piperazin-1-yl | MS calcd for $C_{34}H_{35}F_2N_3 \cdot H^+$ m/z=524 observed m/z=524 $(M+1)^+$ |
| 3an | [1,4'-bipiperidin]-1'-yl | MS calcd for $C_{27}H_{37}N_3 \cdot H^+$ m/z=404 observed m/z=404 $(M+1)^+$ |
| 3ao | 4-benzylpiperazin-1-yl | MS calcd for $C_{28}H_{33}N_3 \cdot H^+$ m/z=412 observed m/z=412 $(M+1)^+$ |

EXAMPLE 4

The following azetidines were prepared by the reductive amination route of Example 3, starting with 1-benzhydryl-3-azetidinone:

| Ex. | R₇ | Analytical Data |
|---|---|---|
| 4a | 1,2,3,4-tetrahydronaphthalen-1-yl | MS calcd for $C_{26}H_{28}N_2 \cdot H^+$ m/z=369 observed m/z=369 $(M+1)^+$ |
| 4b | 2-(2-chlorophenyl)ethyl | MS calcd for $C_{24}H_{25}ClN_2 \cdot H^+$ m/z=377 observed m/z=377 $(M+1)^+$ |
| 4c | 2-chlorobenzyl | MS calcd for $C_{23}H_{23}ClN_2 \cdot H^+$ m/z=363 observed m/z=363 $(M+1)^+$ |
| 4d | benzyl | MS calcd for $C_{23}H_{24}N_2 \cdot H^+$ m/z=329 observed m/z=329 $(M+1)^+$ |
| 4e | 3-chlorobenzyl | MS calcd for $C_{23}H_{23}ClN_2 \cdot H^+$ m/z=363 observed m/z=363 $(M+1)^+$ |
| 4f | 2-(2-methoxyphenyl)ethyl | MS calcd for $C_{25}H_{28}N_2O \cdot H^+$ m/z=373 observed m/z=373 $(M+1)^+$ |
| 4g | 2-phenylethyl | MS calcd for $C_{24}H_{26}N_2 \cdot H^+$ m/z=343 observed m/z=343 $(M+1)^+$ |
| 4h | 2-(4-methoxyphenyl)ethyl | MS calcd for $C_{25}H_{28}N_2O \cdot H^+$ m/z=373 observed m/z=373 $(M+1)^+$ |
| 4i | 3-(trifluoromethyl)benzyl | MS calcd for $C_{24}H_{23}F_3N_2 \cdot H^+$ m/z=397 observed m/z=397 $(M+1)^+$ |
| 4j | 4-chlorobenzyl | MS calcd for $C_{23}H_{23}ClN_2 \cdot H^+$ m/z=363 observed m/z=363 $(M+1)^+$ |
| 4k | 2-(4-chlorophenyl)ethyl | MS calcd for $C_{24}H_{25}ClN_2 \cdot H^+$ m/z=377 observed m/z=377 $(M+1)^+$ |
| 4l | Ph(CH₂)₄ | MS calcd for $C_{26}H_{30}N_2 \cdot H^+$ m/z=371 observed m/z=371 $(M+1)^+$ |

-continued

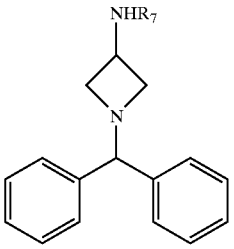

| Ex. | R₇ | Analytical Data |
|---|---|---|
| 4m | 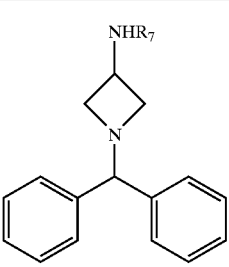 | MS calcd for $C_{23}H_{22}ClFN_2 \cdot H^+$ m/z=381 observed m/z=381 $(M+1)^+$ |
| 4n | 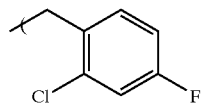 | MS calcd for $C_{24}H_{25}ClN_2 \cdot H^+$ m/z=377 observed m/z=377 $(M+1)^+$ |
| 4o | 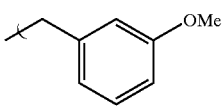 | MS calcd for $H_{31}H_{32}N_2 \cdot H^+$ m/z=433 observed m/z=433 $(M+1)^+$ |
| 4p | 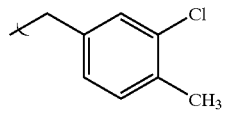 | MS calcd for $C_{23}H_{22}Cl_2N_2 \cdot H^+$ m/z=397 observed m/z=397 $(M+1)^+$ |
| 4q | 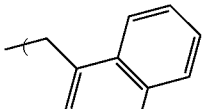 | MS calcd for $C_{23}H_{30}N_2 \cdot H^+$ m/z=335 observed m/z=335 $(M+1)^+$ |
| 4r | $C_{10}H_{21}$-n | MS calcd for $C_{26}H_{38}N_2 \cdot H^+$ m/z=379 observed m/z=379 $(M+1)^+$ |
| 4s | 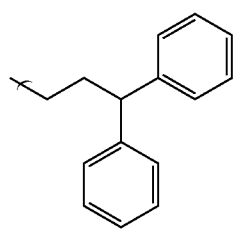 | MS calcd for $C_{24}H_{24}N_2O_2 \cdot H^+$ m/z=373 observed m/z=373 $(M+1)^+$ |
| 4t | 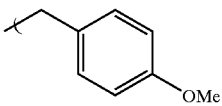 | MS calcd for $C_{21}H_{22}N_2O \cdot H^+$ m/z=319 observed m/z=319 $(M+1)^+$ |
| 4u | 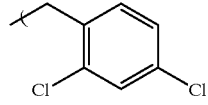 | MS calcd for $C_{24}H_{23}F_3N_2 \cdot H^+$ m/z=397 observed m/z=397 $(M+1)^+$ |
| 4v | 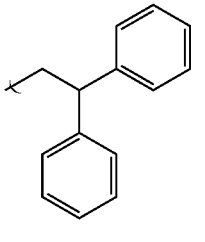 | MS calcd for $C_{24}H_{25}ClN_2 \cdot H^+$ m/z=377 observed m/z=377 $(M+1)^+$ |

-continued

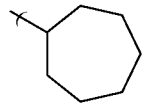

| Ex. | R₇ | Analytical Data |
|---|---|---|
| 4w | 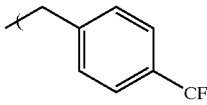 | MS calcd for $C_{24}H_{26}N_2O \cdot H^+$ m/z=359 observed m/z=359 $(M+1)^+$ |
| 4x |  | MS calcd for $C_{27}H_{26}N_2 \cdot H^+$ m/z=379 observed m/z=379 $(M+1)^+$ |
| 4y | 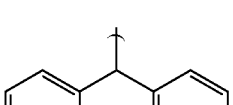 | MS calcd for $C_{24}H_{26}N_2O \cdot H^+$ m/z=359 observed m/z=359 $(M+1)^+$ |
| 4z | 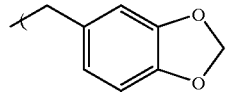 | MS calcd for $C_{30}H_{30}N_2 \cdot H^+$ m/z=419 observed m/z=419 $(M+1)^+$ |
| 4aa | 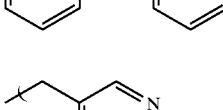 | MS calcd for $C_{24}H_{23}F_3N_2 \cdot H^+$ m/z=397 observed m/z=397 $(M+1)^+$ |
| 4ab | 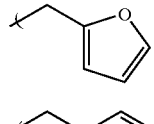 | MS calcd for $C_{29}H_{28}N_2 \cdot H^+$ m/z=405 observed m/z=405 $(M+1)^+$ |
| 4ac | 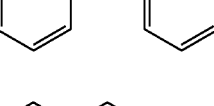 | MS calcd for $C_{22}H_{23}N_3 \cdot H^+$ m/z=330 observed m/z=330 $(M+1)^+$ |

-continued

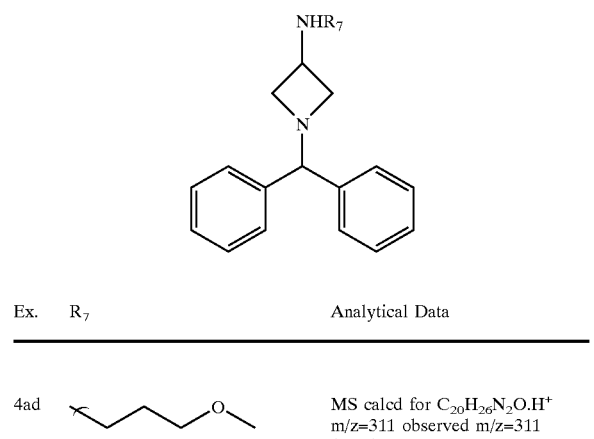

| Ex. | R7 | Analytical Data |
|---|---|---|
| 4ad | ~~~O~Me | MS calcd for $C_{20}H_{26}N_2O.H^+$ m/z=311 observed m/z=311 $(M+1)^+$ |

-continued

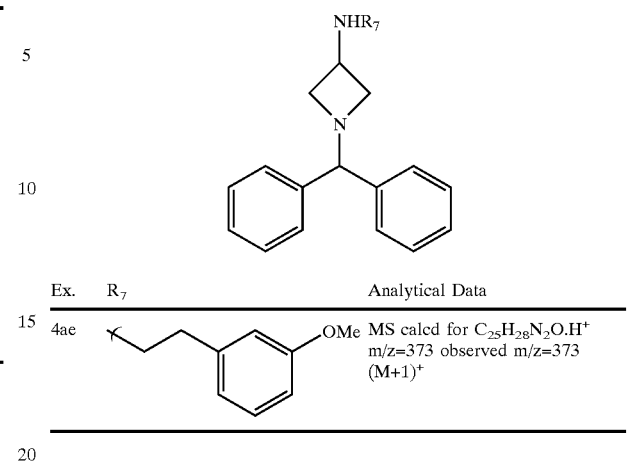

| Ex. | R7 | Analytical Data |
|---|---|---|
| 4ae | ~~~(3-OMe-phenyl)ethyl | MS calcd for $C_{25}H_{28}N_2O.H^+$ m/z=373 observed m/z=373 $(M+1)^+$ |

In a similar manner, the following secondary amines were prepared:

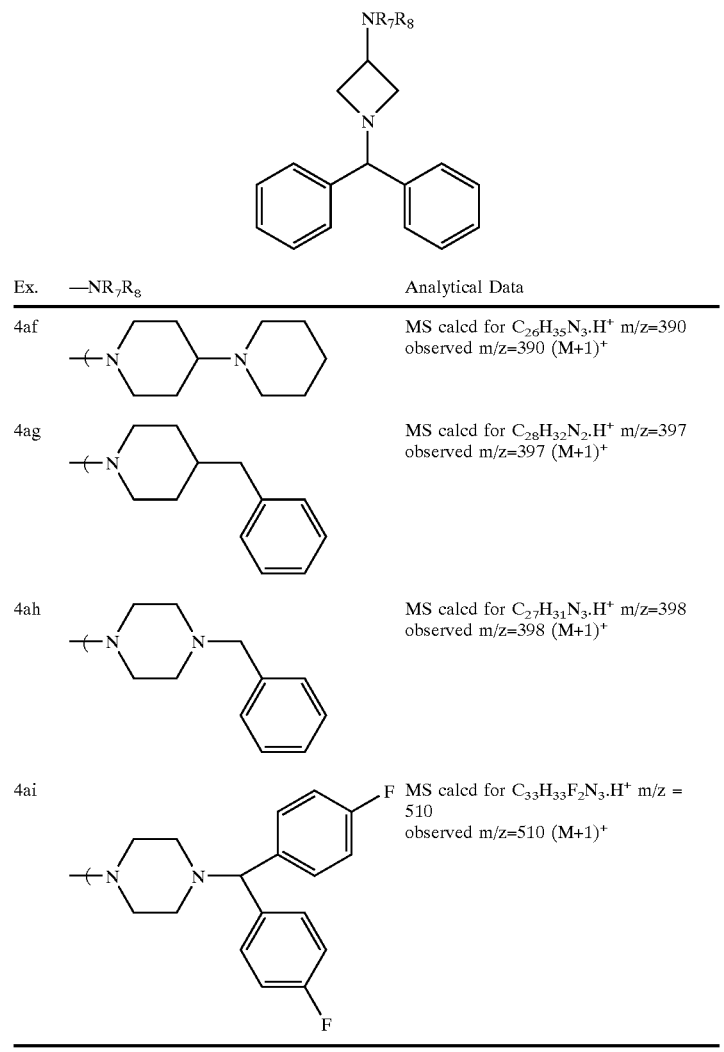

| Ex. | —NR7R8 | Analytical Data |
|---|---|---|
| 4af | 4-piperidinylpiperidine | MS calcd for $C_{26}H_{35}N_3.H^+$ m/z=390 observed m/z=390 $(M+1)^+$ |
| 4ag | 4-benzylpiperidine | MS calcd for $C_{26}H_{32}N_2.H^+$ m/z=397 observed m/z=397 $(M+1)^+$ |
| 4ah | 4-benzylpiperazine | MS calcd for $C_{27}H_{31}N_3.H^+$ m/z=398 observed m/z=398 $(M+1)^+$ |
| 4ai | 4-[bis(4-fluorophenyl)methyl]piperazine | MS calcd for $C_{33}H_{33}F_2N_3.H^+$ m/z = 510 observed m/z=510 $(M+1)^+$ |

EXAMPLE 5

The following diazetidines were prepared by the reductive amination route of Example 3:

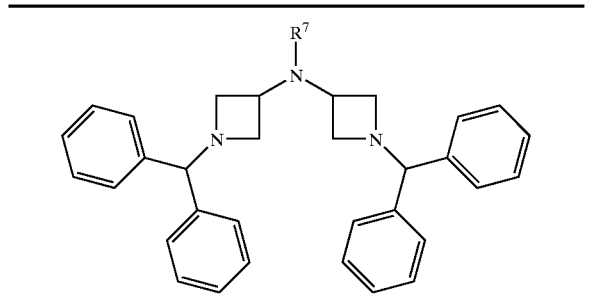

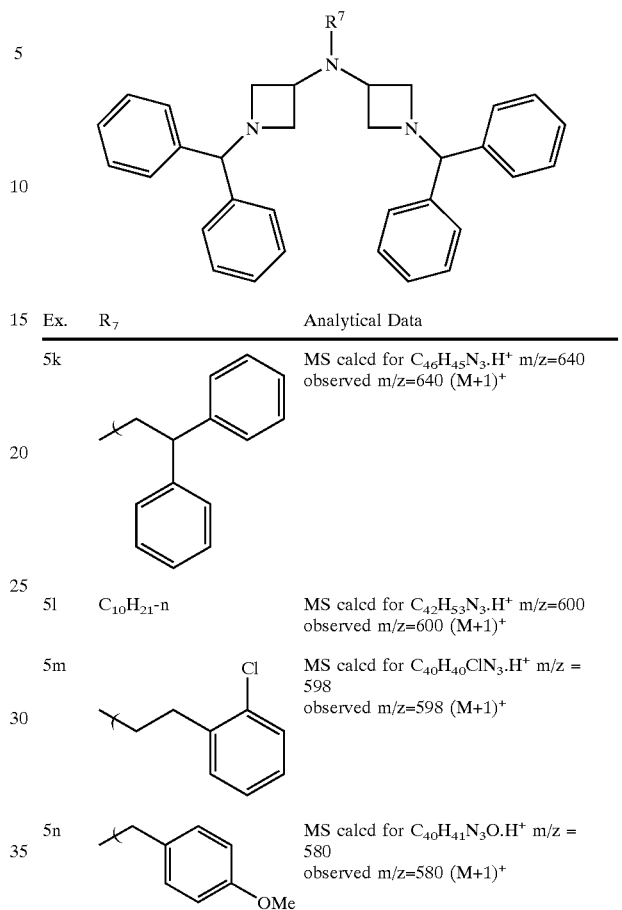

| Ex. | R7 | Analytical Data |
|---|---|---|
| 5a | (tetrahydronaphthalenyl) | MS calcd for $C_{42}H_{43}N_3.H^+$ m/z=590<br>observed m/z=590 (M+1)$^+$ |
| 5b | (imidazolyl-propyl) | MS calcd for $C_{38}H_{41}N_5.H^+$ m/z=568<br>observed m/z=568 (M+1)$^+$ |
| 5c | (naphthylmethyl) | MS calcd for $C_{43}H_{41}N_3.H^+$ m/z=600<br>observed m/z=600 (M+1)$^+$ |
| 5d | (3-CF3-benzyl) | MS calcd for $C_{40}H_{38}F_3N_3.H^+$ m/z = 618<br>observed m/z=618 (M+1)$^+$ |
| 5e | (3-pyridylmethyl) | MS calcd for $C_{38}H_{38}N_4.H^+$ m/z=551<br>observed m/z=551 (M+1)$^+$ |
| 5f | (4-pyridylmethyl) | MS calcd for $C_{38}H_{38}N_4.H^+$ m/z=551<br>observed m/z=551 (M+1)$^+$ |
| 5g | (pyrrolidinonyl-propyl) | MS calcd for $C_{39}H_{44}N_4O.H^+$ m/z = 585<br>observed m/z=585 (M+1)$^+$ |
| 5h | (benzodioxolylmethyl) | MS calcd for $C_{40}H_{39}N_3O_2.H^+$ m/z = 594<br>observed m/z=594 (M+1)$^+$ |
| 5i | (methoxypropyl) | MS calcd for $C_{36}H_{41}N_3O.H^+$ m/z = 532<br>observed m/z=532 (M+1)$^+$ |
| 5j | (phenylethyl) | MS calcd for $C_{40}H_{41}N_3.H^+$ m/z=564<br>observed m/z=564 (M+1)$^+$ |
| 5k | (diphenylethyl) | MS calcd for $C_{46}H_{45}N_3.H^+$ m/z=640<br>observed m/z=640 (M+1)$^+$ |
| 5l | $C_{10}H_{21}$-n | MS calcd for $C_{42}H_{53}N_3.H^+$ m/z=600<br>observed m/z=600 (M+1)$^+$ |
| 5m | (2-Cl-phenylethyl) | MS calcd for $C_{40}H_{40}ClN_3.H^+$ m/z = 598<br>observed m/z=598 (M+1)$^+$ |
| 5n | (4-OMe-benzyl) | MS calcd for $C_{40}H_{41}N_3O.H^+$ m/z = 580<br>observed m/z=580 (M+1)$^+$ |

Biological Activity of the Compounds

Nociceptin Binding Assay:

CHO cell membrane preparation expressing the ORL-1 receptor (2 mg) was incubated with varying concentrations of [$I^{125}$][Tyr$^{14}$]nociceptin (3–500 pM) in a buffer containing 50 mM HEPES (pH7.4), 10 mM NaCl, 1 mM MgCl$_2$, 1 mg/ml bovine serum albumin and 0.025% bacitacin. In a number of studies, assays were carried out in buffer 50 mM tris-HCl (pH7.4), 1 mg/ml bovine serum albumin and 0.025% bacitracin. Samples were incubated for 1 h at room temperature (22° C.). Radiolabelled ligand bound to the membrane was harvested over GF/B filters presoaked with 0.1% polyethyleneimine using a Brandell cell harvester and washed five times with 5 ml cold distilled water. Nonspecific binding was determined in parallel by similar assays performed in the presence of 1 $\mu$M nociceptin. All assay points were performed in duplicates of total and nonspecific binding. Calculations of $K_i$ were made using methods well known in the art.

For compounds of this invention, $K_i$ values were determined to be in the range of about 0.009 to about 50 $\mu$M, with compounds having a $K_i$ value in the range of about 0.009 to about 0.500 $\mu$M being preferred.

Agonist Activity

Using the procedures described the *European Journal of Pharmacology*, 336 (1997), p. 233–242, the agonist activity of compounds of the invention are determined.

Cough Studies

The effect of compounds of formula I are evaluated in capsaicin-induced cough in the guinea pig according to the methods of Bolser et al. *British Journal of Pharmacology* (1995) 114, 735–738. This model is a widely used method to evaluate the activity of potential antitussive drugs. Overnight fasted male Hartley guinea pigs (350–450 g, Charles River, Bloomington, Mass., USA) are placed in a 12"×14" transparent chamber. The animals are exposed to aerosolized capsaicin (300 μM, for 4 min) produced by a jet nebulizer (Puritan Bennett, Lenexa, Kans., USA) to elicit the cough reflex. Each guinea pig is exposed only once to capsaicin. The number of coughs are detected by a microphone placed in the chamber and verified by a trained observer. The signal from the microphone is relayed to a polygraph which provides a record of the number of coughs. Either vehicle (methylcellulose 1 ml/kg, p.o.) or test compound is given 2 hours before aerosolized capsaicin. The antitussive activity of baclofen (3 mg/kg, p.o.) is also tested as a positive control.

Respiratory Measurements

Studies are performed on male Hartley guinea pigs ranging in weight from 450 to 550 g. The animals are fasted overnight but given water and libitum. The guinea pigs are placed in a whole-body, head-out plethysmograph and a rubber collar is placed over the animal's head to provide an airtight seal between the guinea pig and the plethysmograph. Airflow is measured as a differential pressure across a wire mesh screen which covered a 1-in hole in the wall of the plethysmograph. The airflow signal is integrated to a signal proportional to volume using a preamplifier circuit and a pulmonary function computer (Buxco Electronics, Sharon, Conn., model XA). A head chamber is attached to the plethysmograph and air from a compressed gas source (21% $O_2$, balance $N_2$) is circulated through the head chamber for the duration of study. All respiratory measurements are made while the guinea pigs breathe this circulating air.

The volume signal from each animal is fed into a data acquisition/analysis system (Buxco Electronics, model XA) that calculates tidal volume and respiratory rate on a breath-by-breath basis. These signals are visually displayed on a monitor. Tidal volume and respiratory rate are recorded as an average value every minute.

The guinea pigs are allowed to equilibrate in the plethysmograph for 30 min. Baseline measurements are obtained at the end of this 30 min period. The guinea pigs are then removed from the plethysmograph and orally dosed with test compound (e.g., 10 mg/kg, p.o.), baclofen (3 mg/kg, p.o.) or a methylcellulose vehicle placebo (2 ml/kg, p.o.). Immediately after dosing, the guinea pigs are placed into the plethysmograph, the head chamber and circulating air are reconnected and respiratory variables are measured at 30, 60, 90 and 120 min post treatment. This study is performed under ACUC protocol #960103.

Data Analysis

The data for tidal volume ($V_T$), respiratory rate (f) and minute volume (MV=$V_T$×f) are made for the baseline condition and at each time point after the drug or vehicle. The results are expressed as the mean±SEM.

One to three compounds of formula I can be administered in the method of this invention, preferably one.

For mammals treated for coughing, the nociceptin receptor ORL-1 agonists of formula I may be administered along with one or more additional agents for treating cough, allergy or asthma symptoms selected from antihistamines, 5-lipoxygenase inhibitors, leukotriene inhibitors, $H_3$ inhibitors, β-adrenergic receptor agonists, xanthine derivatives, β-adrenergic receptor agonists, mast cell stabilizers, anti-tussives, expectorants, $NK_1$, $NK_2$ and $NK_3$ tachykinin receptor antagonists, and $GABA_B$ agonists. One to three additional agents can be combined with a compound of formula I, preferably one or two, more preferably one.

Non limitative examples of antihistamines include: astemizole, azatadine, azelastine, acrivastine, brompheniramine, certirizine, chlorpheniramine, clemastine, cyclizine, carebastine, cyproheptadine, carbinoxamine, descarboethoxyloratadine (also known as SCH-34117), doxylamine, dimethindene, ebastine, epinastine, efletirizine, fexofenadine, hydroxyzine, ketotifen, loratadine, levocabastine, mizolastine, equitazine, mianserin, noberastine, meclizine, norastemizole, picumast, pyrilamine, promethazine, terfenadine, tripelennamine, temelastine, trimeprazine and triprolidine.

Non-limitative examples of histamine $H_3$ receptor antagonists include: thioperamide, impromidine, burimamide, clobenpropit, impentamine, mifetidine, S-sopromidine, R-sopromidine, SKF-91486, GR-175737, GT-2016, UCL-1199 and clozapine. Other compounds can readily be evaluated to determine activity at $H_3$ receptors by known methods, including the guinea pig brain membrane assay and the guinea pig neuronal ileum contraction assay, both of which are described in U.S. Pat. No. 5,352,707. Another useful assay utilizes rat brain membranes and is described by West et al., "Identification of Two-$H_3$-Histamine Receptor Subtypes," *Molecular Pharmacology*, Vol. 38, pages 610–613 (1990).

The term "leukotriene inhibitor" includes any agent or compound that inhibits, restrains, retards or otherwise interacts with the action or activity of leukotrienes. Non-limitative examples of leukotriene inhibitors include montelukast [R-(E)]-1[[[1-[3-[2-(7-chloro-2-quinolinyl)-ethenyl]phenyl]-3[2-(1-hydroxy-1-methylethyl)phenyl]propyl]thio]-methyl]cyclopropaneacetic acid and its sodium salt, described in EP 0 480 717; 1-(((R)-(3-(2-(6,7-difluoro-2-quinolinyl)ethenyl)phenyl)-3-(2-(2-hydroxy-2-propyl)phenyl)thio)methylcyclopropaneacetic acid, and its sodium salt, described in WO 97/28797 and U.S. Pat. No. 5,270,324; 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid, and its sodium salt, described in WO 97/28797 and U.S. Pat. No. 5,472,964; pranlukast, N-[4-oxo-2-(1H-tetrazol-5-yl)-4H-1-benzopyran-8-yl]-p-4-phenylbutoxy) benzamide) described in WO 97/28797 and EP 173,516; zafirlukast, (cyclopentyl-3-[2-methoxy-4-[(o-tolylsulfonyl)carbamoyl]benzyl]-1-methylindole-5-carbamate) described in WO 97/28797 and EP 199,543; and [2-[[2(4-tert-butyl-2-thiazolyl)-5-benzofuranyl]oxymethyl]phenyl]acetic acid, described in U.S. Pat. No. 5,296,495 and Japanese patent JP08325265 A.

The term "5-lipoxygenase inhibitor" or "5-LO inhibitor" includes any agent or compound that inhibits, restrains, retards or otherwise interacts with the enzymatic action of 5-lipoxygenase. Non-limitative examples of 5-lipoxygenase inhibitors include zileuton, docebenone, piripost, ICI-D2318, and ABT 761.

Non-limitative examples of β-adrenergic receptor agonists include: albuterol, bitolterol, isoetharine, mataproterenol, perbuterol, salmeterol, terbutaline, isoproterenol, ephedrine and epinephrine.

A non-limitative example of a xanthine derivative is theophylline.

Non-limitative examples of α-adrenergic receptor agonists include arylalkylamines, (e.g., phenylpropanolamine and pseudephedrine), imidazoles (e.g., naphazoline, oxymetazoline, tetrahydrozoline, and xylometazoline), and cycloalkylamines (e.g., propylhexedrine).

A non-limitative example of a mast cell stabilizer is nedocromil sodium.

Non-limitative examples of anti-tussive agents include codeine, dextromethorphan, benzonatate, chlophedianol, and noscapine.

A non-limitative example of an expectorant is guaifenesin.

Non-limitative examples of $NK_1$, $NK_2$ and $NK_3$ tachykinin receptor antagonists include CP-99,994 and SR 48968.

Non-limitatve examples of $GABA_B$ agonists include baclofen and 3-aminopropyl-phosphinic acid.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to provide relief from pain, anxiety, depression, asthma or alcohol abuse. The compounds are non-toxic when administered within this dosage range.

For treating cough, the amount of nociceptin receptor ORL-1 agonist in a unit dose is preferably from about 0.1 mg to 1000 mg, more preferably, from about 1 mg to 300 mg. A typical recommended dosage regimen is oral administration of from 1 mg to 2000 mg/day, preferably 1 to 1000 mg/day, in two to four divided doses. When treating coughing, the nociceptin receptor ORL-1 agonist may be administered with one or more additional agents for treating cough, allergy or asthma symptoms selected from the group consisting of: antihistamines, 5-lipoxygenase inhibitors, leukotriene inhibitors, $H_3$ inhibitors, $\beta$-adrenergic receptor agonists, xanthine derivatives, $\alpha$-adrenergic receptor agonists, mast cell stabilizers, anti-tussives, expectorants, $NK_1$, $NK_2$ and $NK_3$ tachykinin receptor antagonists, and $GABA_B$ agonists. The nociceptin receptor ORL-1 agonist and the additional agents are preferably administered in a combined dosage form (e.g., a single tablet), although they can be administered separately. The additional agents are administered in amounts effective to provide relief from cough, allergy or asthma symptoms, preferably from about 0.1 mg to 1000 mg, more preferably from about 1 mg to 300 mg per unit dose. A typical recommended dosage regimen of the additional agent is from 1 mg to 2000 mg/day, preferably 1 to 1000 mg/day, in two to four divided doses.

The following are examples of pharmaceutical dosage forms which contain a compound of the invention. The scope of the invention in its pharmaceutical composition aspect is not to be limited by the examples provided.

Pharmaceutical Dosage Form Examples

Example A-Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|   | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B-Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|   | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the formula

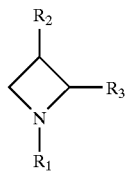

or a pharmaceutically acceptable salt or solvate thereof, or a diastereomer or enantiomer thereof, wherein:

(a) $R_1$ is —$(CH_2)_n CHR_4R_5$, fluorenyl, pyrimidinyl or

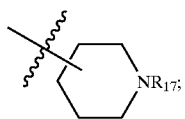

n is 0, 1, 2 or 3;

$R_2$ is H; and $R_3$ is —C(H)(R)—$NR_7R_8$;

R is H, aryl, $R_6$-aryl, aryl$(CH_2)_{1-2}$, $R_6$-aryl$(CH_2)_{1-2}$ or heteroaryl;

$R_4$ is H, aryl, $R_6$-aryl, heteroaryl, $C_{1-6}$ alkyl, $C_{3-6}$ cycloalkyl or $C_{2-6}$ alkenyl;

$R_5$ is aryl, $R_6$-aryl, heteroaryl, $C_{1-6}$ alkyl, $C_{3-6}$ cycloalkyl, $C_{2-6}$ alkenyl or fluorenyl, provided that when $R_4$ and $R_5$ are each phenyl, R is not phenyl or $R_6$-phenyl;

or $R_4$ is H and $R_5$ is tetrahydronaphthyl or tetrahydronaphthyl substituted with 1 or 2 substituents selected from the group consisting of halogen, $C_{1-6}$ alkoxy, hydroxy, $C_{1-6}$ alkyl and trihalo$(C_{1-6})$alkyl;

$R_6$ is 1 or 2 substituents independently selected from the group consisting of halogen, $C_{1-6}$alkoxy, hydroxy, phenyl, phenoxy, $C_{1-6}$alkyl, trihalo$(C_{16})$alkyl, amino, amido, —$NO_2$, naphthyl, benzoyl and benzyloxy, or 2 adjacent ring carbon atoms can be substituted by methylenedioxy;

$R_7$ is —$(CH_2)_xR_9$, tetrahydronaphthyl, tetrahydronaphthyl substituted with 1 or 2 $R_{10}$ groups, or $C_5$–$C_7$ cycloalkyl; and $R^8$ is H;

or $R_7$ and $R_8$ together form a ring of the formula

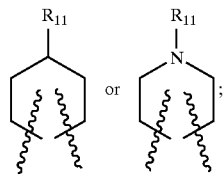

x is 0 to 10;

$R_9$ is H, $C_1$–$C_6$ alkoxy, phenyl, phenyl substituted with 1 or 2 $R_{10}$ groups, naphthyl, pyridyl, imidazolyl, furanyl, pyrrolidinyl, pyrrolidonyl, piperidinyl, N—($C_1$–$C_6$ alkyl)-piperidinyl, N-aryl($C_1$–$C_6$ alkyl)piperidinyl or diphenylmethyl;

$R_{10}$ is independently selected from the group consisting of halogen, $C_1$–$C_6$ alkoxy, $C_1$–$C_6$ alkyl, —$OCF_3$ and methylenedioxy;

$R_{11}$ is aryl($C_1$–$C_6$)alkyl, di-aryl($C_1$–$C_6$)alkyl or piperidinyl; and $R_{17}$ is H, $C_1$–$C_6$ alkyl or benzyl; or (b) $R_2$ is —$NHR_7$ or

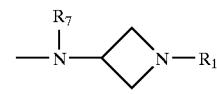

and $R_3$ is H; and $R_1$ and $R_7$ are as defined in (a).

2. The compound of claim 1 wherein $R_1$ is —$(CH_2)_n CHR_4R_5$ and n is 0 or 1.

3. The compound of claim 2 wherein $R_4$ is aryl, $R_6$-aryl or heteroaryl and $R_5$ is aryl or $C_1$–$C_6$ alkyl.

4. The compound of claim 3 wherein n is 0, $R_4$ is phenyl, $R_6$-phenyl or pyridyl and $R_5$ is phenyl, $R_6$-phenyl or $C_2$–$C_5$ alkyl.

5. The compound of claim 4 wherein $R_6$ is halogen.

6. The compound of claim 1 wherein $R_2$ is H and $R_3$ is —C(H)(R)—$NR_7R_8$.

7. The compound of claim 6 wherein R is $R_6$-phenyl, benzyl or $R_6$-benzyl.

8. The compound of claim 7 wherein $R_6$ is 1 or 2 substituents independently selected from the group consisting of —$CF_3$, halogen, benzyloxy and —$CH_3$.

9. The compound of claim 7 wherein $R_7$ and $R_8$ are each H.

10. The compound of claim 1 selected from the group consisting of

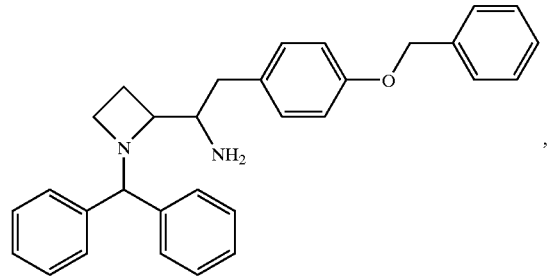

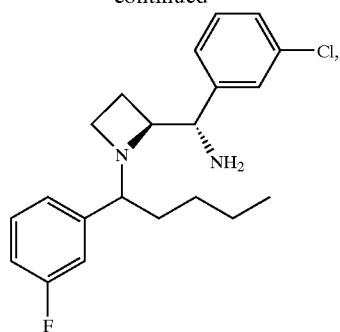
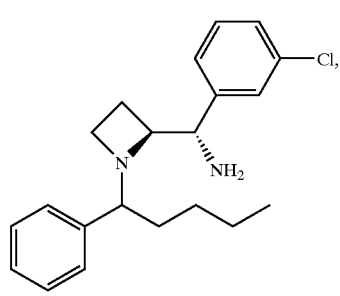
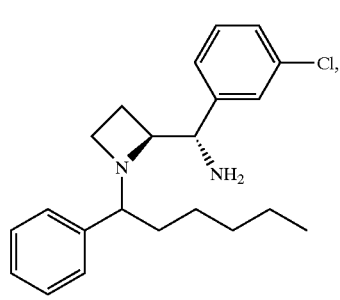
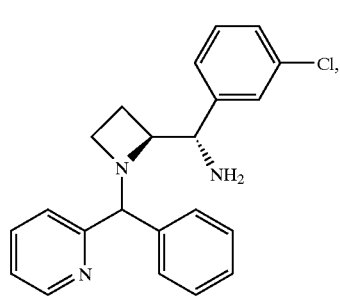
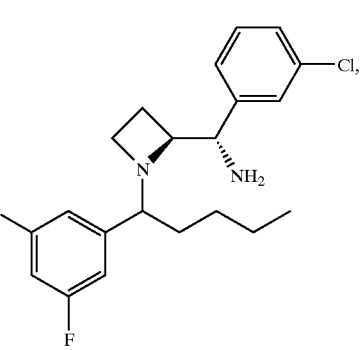
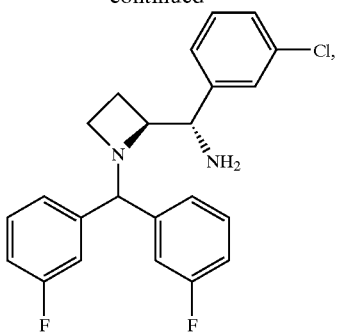
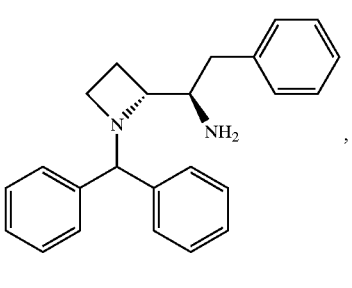
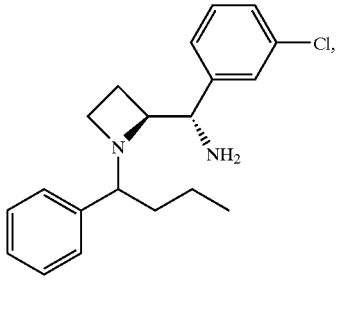
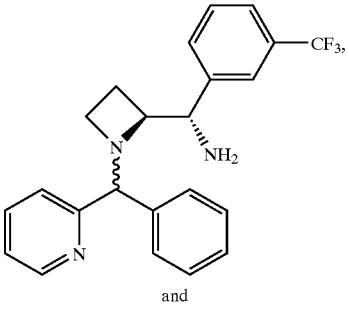
and
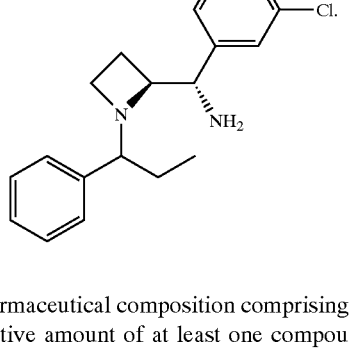
11. A pharmaceutical composition comprising a therapeutically effective amount of at least one compound of claim 1 in combination with a pharmaceutically acceptable carrier.

12. A pharmaceutical composition comprising: a therapeutically effective amount of at least one compound of claim 1; a therapeutically effective amount of one or more additional agents selected from the group consisting of: antihistamines, 5-lipoxy-genase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists; and a pharmaceutically acceptable carrier.

13. A method of treating cough, pain, anxiety, asthma, depression or alcohol abuse comprising administering an effective amount of at least one compound of claim 1 to a mammal in need of such treatment.

14. The method of claim 13, wherein in addition to at least one compound of claim 1, an effective amount of one or more additional agents for treating cough, allergy or asthma symptoms selected from the group consisting of: antihistamines, 5-lipoxy-genase inhibitors, leukotriene inhibitors, $H_3$ inhibitors, β-adrenergic receptor agonists, xanthine derivatives, α-adrenergic receptor agonists, mast cell stabilizers, anti-tussives, expectorants, $NK_1$, $NK_2$ and $NK_3$ tachykinin receptor antagonists, and $GABA_B$ agonists is administered.

* * * * *